United States Patent
Kusukame et al.

(10) Patent No.: US 9,322,716 B2
(45) Date of Patent: Apr. 26, 2016

(54) COMPONENT MEASURING APPARATUS AND MOVING BODY

(71) Applicant: Panasonic Intellectual Property Corporation of America, Torrance, CA (US)

(72) Inventors: Koichi Kusukame, Nara (JP); Tatsuo Itoh, Osaka (JP); Kazuki Funase, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 0 days.

(21) Appl. No.: 14/576,191

(22) Filed: Dec. 18, 2014

(65) Prior Publication Data
US 2015/0192466 A1   Jul. 9, 2015

(30) Foreign Application Priority Data
Jan. 7, 2014   (JP) .................................. 2014-001124

(51) Int. Cl.
G01J 5/20      (2006.01)
G01J 5/60      (2006.01)
G01N 21/35     (2014.01)
G01N 21/3554   (2014.01)

(52) U.S. Cl.
CPC . *G01J 5/60* (2013.01); *G01N 21/35* (2013.01); *G01N 21/3554* (2013.01); *G01J 2005/607* (2013.01)

(58) Field of Classification Search
CPC .................................................. G01N 21/3504
See application file for complete search history.

(56) References Cited

U.S. PATENT DOCUMENTS

| | | | | | |
|---|---|---|---|---|---|
| 5,466,425 | A | * | 11/1995 | Adams | A61L 2/02 210/243 |
| 6,344,175 | B1 | * | 2/2002 | Akae | F23G 5/085 204/157.15 |
| 6,853,452 | B1 | * | 2/2005 | Laufer | G01N 21/3504 356/436 |
| 2007/0208238 | A1 | * | 9/2007 | Harjunmaa | A61B 5/14532 600/316 |
| 2014/0305190 | A1 | * | 10/2014 | Okamoto | G01N 33/004 73/23.31 |

FOREIGN PATENT DOCUMENTS

| | | | |
|---|---|---|---|
| CN | 102818606 A | * | 12/2012 |
| JP | 2004245820 A | * | 9/2004 |
| JP | 2010-025622 | | 2/2010 |
| JP | 2012-154854 | | 8/2012 |
| KR | 20030067464 A | * | 8/2003 |

\* cited by examiner

*Primary Examiner* — Kiho Kim
(74) *Attorney, Agent, or Firm* — Greenblum & Bernstein, P.L.C.

(57) ABSTRACT

A component measuring apparatus includes a plurality of light sources having different Wavelengths. The component measuring apparatus also includes an irradiation unit that applies lights emitted from the plural light sources to a measurement object, and a light receiving unit that receives at least one of light having transmitted through the measurement object and light having been scattered from the measurement object. The component measuring apparatus further includes a measuring unit that measures intensity of the light received by the light receiving unit per wavelength.

13 Claims, 12 Drawing Sheets

COMPONENT MEASURING APPARATUS AND MOVING BODY

CROSS REFERENCES TO RELATED APPLICATIONS

This application claims priority to Japanese Patent Application No. 2014-001124, filed on Jan. 7, 2014, the contents of which are hereby incorporated by reference.

BACKGROUND

1. Technical Field

The present disclosure relates to a component measuring apparatus and a moving body, which measure a distribution (density or concentration distribution) of a specific component by spectrometry that provides a simple absorption spectrum.

2. Description of the Related Art

In related-art component measuring apparatuses utilizing spectrometry, a lamp or a ceramic heater is used as a light source, and light having transmitted through a measurement object or light having been reflected from a measurement object is subjected to spectrometry with a diffraction grating or through interference.

In an example of a component measuring apparatus for detecting the presence or the absence of a measurement object, a two-dimensional distribution of the measurement object is visualized by sweeping the wavelength of laser light, and by scanning a surface to be measured. (See, e.g., Japanese Unexamined Patent Application Publication No. 2012-154854.) FIG. 12 illustrates a liquid leakage detection device of related art, which is disclosed in Japanese Unexamined Patent Application Publication No. 2012-154854.

In FIG. 12, a leakage oil detection device 201 applies infrared light 204 in a wavelength range of 2 µm to 25 µm to a surface of an oil enclosure 202 while scanning the infrared light. Furthermore, the wavelength of the applied infrared light is swept over a range including 3.6 µm that is the absorption wavelength of oil. When oil 203 enclosed in the oil enclosure 202 is partly leaked and the above-mentioned infrared light is applied to leaked oil 203a, the intensity of reflected and scattered light is dropped near 3.6 µm due to absorption by the leaked oil 203a. Accordingly, the presence of the leaked oil is detected. In another related-art apparatus for judging a skin moisture distribution, the skin moisture distribution is visualized by applying light in a near infrared range to the skin, capturing reflected light by an infrared camera, and executing arithmetic processing based on both the reflection intensity in a wavelength band where light is more apt to be absorbed by moisture, and the reflection intensity in a wavelength band where an influence of absorption by moisture is small. (See, e.g., Japanese Unexamined Patent Application Publication No. 2010-25622.)

SUMMARY

A component measuring apparatus according to the present disclosure includes a plurality of light sources having different wavelengths, an irradiation unit that applies lights emitted from the plural light sources to a measurement object, a light receiving unit that receives at least one of light having transmitted through the measurement object and light having been scattered from the measurement object, and a measuring unit that measures intensity of the light received by the light receiving unit per wavelength.

With the component measuring apparatus according to the present disclosure, spectrometry and distribution measurement of a measurement object can be performed using a small-sized apparatus.

DETAILED DESCRIPTION

Figure 1:
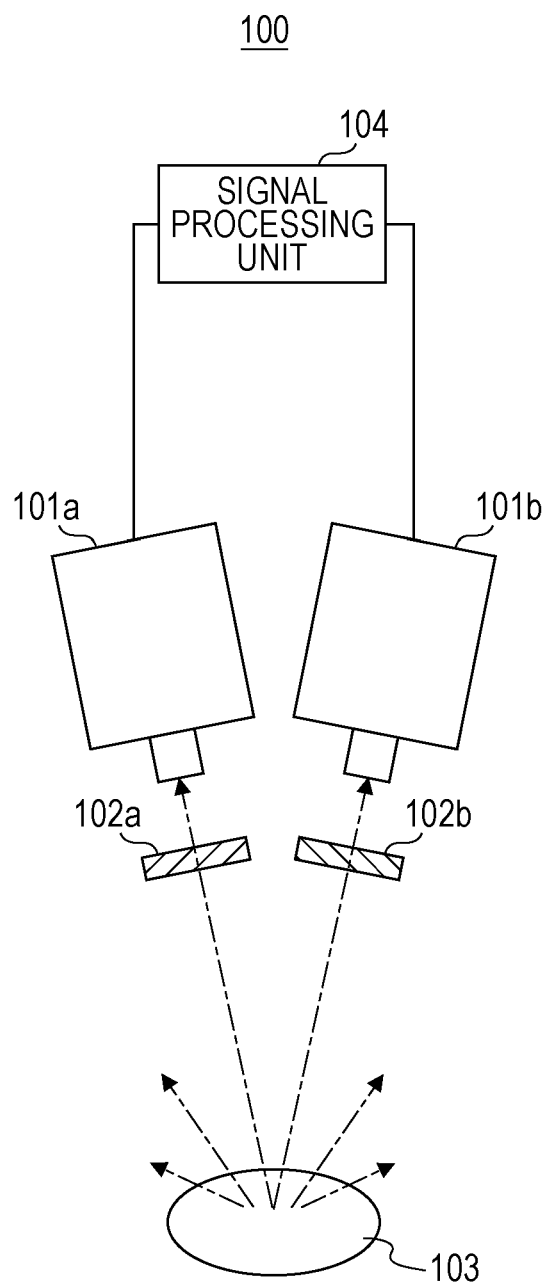
FIG. 1 is a schematic view illustrating one example of a component measuring apparatus according to a first embodiment of the present disclosure.

Prior to explaining embodiments of the present disclosure, the matters having been studied by the inventors are described.

(Underlying Knowledge Forming Basis of the Present Disclosure)

The component measuring apparatus of related art requires a diffraction grating or an interference spectroscopic device. The related-art apparatus for judging a skin moisture distribution requires a halogen lamp with high output power and an infrared camera. Thus, any of those related-art apparatuses have the problem that the apparatus size is large.

The present disclosure provides a component measuring apparatus and a moving body, which have small sizes and which perform spectrometry and distribution measurement of a measurement object.

The component measuring apparatus according to the present disclosure includes a plurality of light sources having different wavelengths, an irradiation unit that applies lights emitted from the plural light sources to a measurement object, a light receiving unit that receives at least one of light having transmitted through the measurement object and light having been scattered from the measurement object, and a measuring unit that measures intensity of the light received by the light receiving unit per wavelength.

With the features described above, spectrometry and measurement of a distribution of the measurement object can be both performed by a small-sized apparatus. Since infrared lights of different wavelengths can be received, a component can be analyzed at high accuracy by comparing the infrared lights of different wavelengths.

The component measuring apparatus may include a unit that receives infrared lights radiated from an object and having different wavelengths, wherein the unit receiving the infrared lights of different wavelengths may be constituted as a plurality of light receiving units that measure respective intensities of the infrared lights of different wavelengths.

The component measuring apparatus may include a unit that receives infrared lights radiated from an object and having different wavelengths, wherein the unit receiving the infrared lights of different wavelengths may include at least one light receiving unit, and a unit that changes the wavelength of the infrared light entering the light receiving unit.

The plural light receiving units may include a first light receiving unit and a second light receiving unit, the first light receiving unit may include a first optical filter allowing infrared light of a first wavelength to pass therethrough, and a first light receiving portion that receives the infrared light having passed through the first optical filter, and the second light receiving unit may include a second optical filter allowing infrared light of a second wavelength to pass therethrough, and a second light receiving portion that receives the infrared light having passed through the second optical filter.

The component measuring apparatus may further include a signal processing unit that identifies the object radiating the infrared lights by obtaining first data related to intensity of the infrared light received by the first light receiving unit and having the first wavelength, and second data related to intensity of the infrared light received by the second light receiving unit and having the second wavelength, and by comparing the first data with the second data.

The signal processing unit may further measure a temperature of the object by employing one of the first data and the second data.

At least one part of the infrared lights of which intensities are measured by the light receiving unit may be infrared light having wavelength of 5 µm or longer and 8 µm or shorter, and at least one of components to be measured may be moisture.

Materials of the light receiving unit may include at least a material mainly containing InSb.

A moving body according to the present may include a moving unit that moves the moving body, a suction unit that sucks air and/or a substance existing outside, and a moisture measuring unit that measures information regarding moisture in an object from received light.

The moisture measuring unit may include a plurality of light sources having different wavelengths, an irradiation unit that applies lights emitted from the plural light sources to a measurement object, a light receiving unit that receives at least one of light having transmitted through the measurement object and light having been scattered from the measurement object, and a measuring unit that measures intensity of the light received by the light receiving unit per wavelength.

The moisture measuring unit may include a unit that receives infrared lights radiated from an object and having different wavelengths, wherein the unit receiving the infrared lights of different wavelengths may be constituted as a plurality of light receiving units that measure respective intensities of the infrared lights of different wavelengths.

The moisture measuring unit may include a unit that receives infrared lights radiated from an object and having different wavelengths, wherein the unit receiving the infrared lights of different wavelengths may include at least one light receiving unit, and a unit that changes the wavelength of the infrared light entering the light receiving unit.

The moving body may further include a humidity measuring unit that measures humidity, and a radiation temperature measuring unit that measures radiation temperature.

The moving body may further include at least one of a drying unit that dries a place where presence of moisture has been confirmed by employing the moisture measuring unit, and a sterilization unit that sterilizes the place where the presence of moisture has been confirmed.

The moving body may further include a notification unit that notifies a user of the place where the presence of moisture has been confirmed by employing the moisture measuring unit.

The suction unit may be disposed inside the moving body and sucks dust and/or dirt through a suction opening formed in the moving body, and the moisture measuring unit may measure moisture in a object that is positioned in a direction different from an advancing direction of the moving body.

The moving body may further include a controller that controls at least one of the moving unit and the suction unit in accordance with the information regarding moisture in the object, which has been measured by the moisture measuring unit, and the controller may execute at least one of two types of control of (i) controlling the moving unit not to move over an object having a certain amount or more of moisture, and (ii) controlling the suction unit not to perform sucking in a region around the object having a certain amount or more of moisture.

The moving body may further include at least one of a radiant heating unit that radiates a far infrared ray, and a blowing unit that blows hot air, wherein the drying is performed by at least one of the radiant heating unit and the blowing unit.

The sterilization by the sterilization unit may be performed by applying an ultraviolet ray or ions.

The notification unit may include a button to be pushed by the user, and when the user pushes the button, the moving body may be moved to a place where moisture is present, the place being recorded in the moving body, thus notifying the user of the place where moisture is present.

The moving body may further include a communication unit that obtains status of use of another device, and a controller that sets at least one of a time at which the moving body is to be moved by the moving unit, and a time at which moisture is to be measured by the moisture measuring unit, in accordance with the status of use of the other device, the status being obtained through the communication unit.

Embodiments of the present disclosure will be described below with reference to the drawings.

A first embodiment is described in connection with examples of a component measuring apparatus that receives infrared light radiated from an object. A second embodiment is described in connection with examples of a component measuring apparatus that applies lights of different wavelengths, and that receives transmitted or scattered light of the applied light. Measurement of a moisture (density) distribution can be practiced as one application example of the component measuring apparatuses according to the first and second embodiments.

As the application example of the measurement of a moisture (density) distribution, one example of a movable sensing unit, which senses a humidity distribution in a room, is described in a third embodiment. One example of a drying control method for sensing a wet state of washing is described in a fourth embodiment. One example of a wet floor (road surface) detecting method for sensing a wet state of a store floor or a road surface is described in a fifth embodiment.

It is to be noted that the following embodiments represent specific examples of the present disclosure. Numerical values, shapes, materials, constituent members, steps, sequences of steps, and so on, which are described in the following embodiments, are merely illustrative, and they are not purported to limit the present disclosure. Among the constituent members in the following embodiments, those ones other than the constituent members not stated in independent claims, which define most significant concepts, are described as optional constituent members. Individual matters described in all the embodiments can be optionally combined with each other.

(First Embodiment)

FIG. 1 is a schematic view illustrating a component measuring apparatus 100 according to the first embodiment of the present disclosure.

The component measuring apparatus 100 according to this embodiment includes a light receiving unit 101a, a light receiving unit 101b, an optical filter 102a, an optical filter 102b, and a signal processing unit 104.

In this embodiment, a substance (or a component) as an object to be identified by the component measuring apparatus 100 is decided in advance.

Referring to FIG. 1, each of reference symbols 101a and 101b denotes a light receiving unit that receives infrared light (or an infrared ray). Reference symbol 102a denotes an optical filter allowing infrared light, which includes wavelength in a particular band (first wavelength band), to pass therethrough.

Reference symbol 102b denotes an optical filter allowing infrared light, which includes wavelength in a particular band (second wavelength band), to pass therethrough. The first wavelength band and the second wavelength band are different from each other.

The light receiving unit 101a receives part of infrared light radiated from a predetermined position (measurement position) of a measurement object 103, the part having passed through the optical filter 102a and including wavelength (first wavelength) in the first wavelength band.

The light receiving unit 101b receives part of the infrared light radiated from the predetermined position (measurement position) of the measurement object 103, the part having passed through the optical filter 102b and including wavelength (second wavelength) in the second wavelength band.

Alternatively, the light receiving units 101a and 101b may receive light, which has transmitted through the measurement object 103, via the optical filters 102a and 102b, respectively.

The optical filters 102a and 102b allow infrared lights in different wavelength bands to pass therethrough.

The first wavelength band is a wavelength band of the infrared light radiated from the substance (or the component) to be identified, the wavelength band being used for example, to specify the substance (or the component) to be identified.

The second wavelength band is a wavelength band used for example, to specify the substance (or the component) to be identified.

When one of intensity of the infrared light including the wavelength (first wavelength) in the first wavelength band and intensity of the infrared light including the wavelength (second wavelength) in the second wavelength band varies depending on a temperature of the substance (or the component) to be identified, the temperature of the substance (or the component) to be identified can be detected by detecting the intensity of the infrared light including the wavelength in the corresponding wavelength band.

This embodiment is described below, by way of example, in connection with the case where the intensity of the infrared light including the wavelength in the second wavelength band varies depending on the temperature of the substance (or the component) to be identified.

The light receiving units 101a and 101b measure the intensities of the infrared lights including the wavelengths in the wavelength bands after having passed through the optical filters 102a and 102b, respectively. Data of the intensities of the infrared lights received by the light receiving units 101a and 101b are sent to the signal processing unit 104.

The signal processing unit 104 discretely determines a spectrum distribution of the infrared light radiated from the measurement object 103 based on the respective intensities of the infrared lights received by the light receiving units 101a and 101b.

For example, the signal processing unit 104 includes a memory (not illustrated) and a processor (not illustrated), such as a central processing unit (CPU). The CPU reads a program from the memory and executes the program. The signal processing unit 104 is realized by the CPU executing the program.

Alternatively, a function of the signal processing unit 104 may be implemented by dedicated hardware circuits (or dedicated hardware circuitry), such as application-specific integrated circuit (ASICs) or field programmable gate arrays (FPGAs).

The memory (not illustrated) in the signal processing unit 104 previously stores identification object information corresponding to information that is related to infrared lights radiated from various substances (or components) to be identified. The identification object information contains, as data, information representing, e.g., a relative relationship between the intensity of partial infrared light including the wavelength in the first wavelength band and the intensity of partial infrared light including the wavelength in the second wavelength band, both the partial infrared lights being parts of the infrared light radiated from the substance to be identified. The information representing the relative relationship is, e.g., a magnitude relationship representing which one is larger or smaller.

For example, when the intensity of partial infrared light being part of the infrared light radiated from the substance to be identified and including the wavelength in the second wavelength band varies depending on the temperature of the substance to be identified, the identification object information may contain, as data, information linking the temperature of the substance to be identified with the intensity of the infrared light radiated at that temperature from the substance to be identified and including the wavelength in the second wavelength band. Furthermore, the above linking information is desirably contained in the identification object information for each of plural different values of the temperature.

The identification object information may contain, as data, a value of light intensity (i.e., a first reference light intensity) obtained when the intensity of the infrared light radiated from the substance to be identified and including the wavelength in the first wavelength band is received by the light receiving unit 101a in advance. Moreover, the identification object information may contain, as data, a value of light intensity (i.e., a second reference light intensity) obtained when the intensity of the infrared light radiated from the substance to be identified and including the wavelength in the second wavelength band is received by the light receiving unit 101b in advance.

For example, when the intensity of partial infrared light being part of the infrared light radiated from the substance to be identified and including the wavelength in the second wavelength band varies depending on the temperature of the substance to be identified, the identification object information may contain, as data, information linking the temperature of the substance to be identified with each of the first reference light intensity and the second reference light intensity at that temperature. Furthermore, such linking information is desirably contained in the identification object information for each of plural different values of the temperature.

The identification object information may contain, as data, information linking the distance from each of the light receiving units 101a and 101b to the measurement object 103, in addition to the above-mentioned temperature, with corresponding one of the first reference light intensity and the second reference light intensity.

Respective values of the first reference light intensity and the second reference light intensity, which are obtained when the distances from the light receiving units 101a and 101b to the measurement object 103 are certain preset distances, may be held. When the distances from the light receiving units 101a and 101b to the measurement object 103 are different from the preset certain distances, the respective values of the first reference light intensity and the second reference light intensity may be each corrected depending on the difference between the preset certain distance and the actual distance.

The reason is that the intensities of the infrared lights radiated from the measurement object 103 and received by the light receiving units 101a and 101b depend on the respective distances from the light receiving units 101a and 101b to the measurement object 103.

Accordingly, the component measuring apparatus desirably includes distance measuring units for measuring the respective distances from the light receiving units 101a and 101b to the measurement object 103.

The identification object information may contain, as data, for example, a spectrum distribution of the infrared light radiated from the substance to be identified. When the infrared light radiated from the substance to be identified is different depending on temperature, the identification object information may contain, as data, information linking the temperature of the substance to be identified with a spectral distribution (particularly, a spectrum distribution in the second wavelength band) of the infrared light radiated at that temperature from the substance to be identified. Furthermore, the above linking information is desirably contained in the identification object information for each of plural different values of the temperature.

The spectrum distribution of the infrared light radiated from the substance to be identified contains, as data, at least a maximum value and a minimum value of the intensity of partial infrared light in the first wavelength band, the partial infrared light being part of the infrared light radiated from the substance.

The spectrum distribution of the infrared light radiated from the substance to be identified contains, as data, at least a maximum value and a minimum value of the intensity of partial infrared light in the second wavelength band, the partial infrared light being part of the infrared light radiated from the substance to be identified.

The identification object information may contain, as data, information linking the distance from each of the light receiving units 101a and 101b to the measurement object 103, in addition to the above-mentioned temperature, with the spectral distribution.

The spectral distribution obtained when the distance from each of the light receiving units 101a and 101b to the measurement object 103 is a preset certain distance may be held. When the distance from each of the light receiving units 101a and 101b to the measurement object 103 is different from the preset certain distance, the spectral distribution may be corrected depending on the difference between the preset certain distance and the actual distance.

The signal processing unit 104 receives, for example, data regarding the intensity of the infrared light (first received-light intensity) radiated from the measurement object 103 and including the wavelength in the first wavelength band, and data regarding the intensity of the infrared light (second received-light intensity) radiated from the measurement object 103 and including the wavelength in the second wavelength band, respectively, from the light receiving units 101a and 101b.

The signal processing unit 104 identifies, with respect to the measured position of the measurement object 103, for example, whether the substance radiating the infrared light is the substance to be identified, based on the identification object information stored in the memory.

Specific examples of identification executed in the signal processing unit 104 are as follows. When the identification object information contains the information representing the relative relationship between the intensity of partial infrared light including the wavelength in the first wavelength band and the intensity of partial infrared light including the wavelength in the second wavelength band, both the partial infrared lights being parts of the infrared light radiated from the substance to be identified, the signal processing unit 104 determines whether the relative relationship stored in the memory is held between the first received-light intensity and the second received-light intensity.

More specifically, when the relative relationship stored in the memory is a magnitude relationship, the signal processing unit 104 compares data (first data) regarding the first received-light intensity with data (second data) regarding the second received-light intensity. Then, the signal processing unit 104 checks whether the magnitude relationship stored in the memory is held between the first received-light intensity and the second received-light intensity. If the magnitude relationship is held, the signal processing unit 104 determines that the substance (or the component) to be identified is contained at the measured position of the measurement object 103. If not so, the signal processing unit 104 determines that the substance (or the component) to be identified is not contained.

When the identification object information contains, as data, the information linking the temperature of the substance to be identified with the intensity of the infrared light radiated at that temperature from the substance to be identified and including the wavelength in the second wavelength band, the temperature of the measurement object 103 at the measured position can be measured from the data (second data) regarding the second received-light intensity by utilizing the above-described linking information.

Other specific examples of the identification executed in the signal processing unit 104 are as follows. When the identification object information contains the first reference light intensity and the second reference light intensity, the signal processing unit 104 calculates an absolute value (first absolute value) of the difference between the first received-light intensity and the first reference light intensity, and further calculates an absolute value (second absolute value) of the difference between the second received-light intensity and the second reference light intensity. If the calculated first absolute value and second absolute value are smaller than respective preset thresholds, the signal processing unit 104 determines that the substance (or the component) to be identified is contained at the measured position of the measurement object 103. If not so, the signal processing unit 104 determines that the substance (or the component) to be identified is not contained.

When the identification object information contains, as data, the information linking the temperature of the substance to be identified with each of the first reference light intensity and the second reference light intensity at that temperature, the signal processing unit 104 specifies, based on the above-described linking information, the second reference light intensity at which the absolute value (second absolute value) of the difference relative to the data (second data) regarding the second received-light intensity is smaller than a preset threshold. The signal processing unit 104 can measure the temperature, which is linked with the specified second reference light intensity, as the temperature of the measurement object 103 at the measured position.

Furthermore, the signal processing unit 104 may specify, from the identification object information, the first reference light intensity that is linked with the specified second reference light intensity, and may calculate the first absolute value and the second absolute value by employing the specified first reference light intensity and second reference light intensity.

When the component measuring apparatus includes the distance measuring units for measuring the respective distances from the light receiving units 101a and 101b to the measurement object 103, the signal processing unit 104 specifies the distances measured by the distance measuring units. Furthermore, the signal processing unit 104 may specify, from the identification object information, the linking information representing the first reference light intensity and the second reference light intensity, which correspond to the specified distances, and may calculate the first absolute value and the second absolute value by employing the specified first reference light intensity and second reference light intensity.

Still other specific examples of the identification executed in the signal processing unit 104 are as follows. When the identification object information contains the spectrum distribution of the infrared light radiated from the substance to be identified, the signal processing unit 104 checks whether a value of the first received-light intensity is included in a range (first range) between the maximum value and the minimum value of the intensity of the partial infrared light in the first wavelength band, the partial infrared light being part of the infrared light radiated from the substance to be identified.

Moreover, the signal processing unit 104 checks whether a value of the second received-light intensity is included in a range (second range) between the maximum value and the minimum value of the intensity of the partial infrared light in the second wavelength band, the partial infrared light being part of the infrared light radiated from the substance to be identified.

When the value of the first received-light intensity is included in the first range and the value of the second received-light intensity is included in the second range, the signal processing unit 104 determines that the substance (or the component) to be identified is contained at the measured position of the measurement object 103. If not so, the signal processing unit 104 determines that the substance (or the component) to be identified is not contained.

When the identification object information contains, as data, the information linking the temperature of the substance to be identified with the spectrum distribution (particularly, the spectrum distribution in the second wavelength band) of the infrared light radiated at that temperature from the substance to be identified, the signal processing unit 104 specifies, based on the above-described linking information, the temperature linked with the spectrum distribution of the infrared light that corresponds to the second range including the second received-light intensity.

The signal processing unit 104 can measure the specified temperature, which is linked with the relevant spectrum distribution, as the temperature of the measurement object 103 at the measured position.

Furthermore, the signal processing unit 104 executes operations of specifying, from the identification object information, the spectrum distribution of the infrared light corresponding to the measured temperature, and identifying the substance to be identified by employing the specified spectrum distribution.

Still other specific examples of the identification executed in the signal processing unit 104 are as follows. When the identification object information contains the spectrum distribution of radiant light radiated from the substance to be identified, the signal processing unit 104 compares the spectrum distribution obtained from the second received-light intensity with the spectrum distribution of the radiant light radiated from the substance to be identified. If it is determined that both the spectrum distributions are equal or close to each other, the signal processing unit 104 determines that the measurement object 103 contains the substance (or the component) to be identified. If not so, the signal processing unit 104 determines that the measurement object 103 does not contain the substance (or the component) to be identified.

When the identification object information contains, as data, the information linking the temperature of the substance to be identified with the spectrum distribution (particularly, the spectrum distribution in the second wavelength band) of the infrared light radiated at that temperature from the substance to be identified, the signal processing unit 104 specifies, based on the above-described linking information, the temperature linked with the spectrum distribution in the second wavelength band, which is the same or close to the second received-light intensity.

The signal processing unit 104 can measure the specified temperature, which is linked with the relevant spectrum distribution, as the temperature of the measurement object 103 at the measured position.

Furthermore, the signal processing unit 104 executes operations of specifying, from the identification object information, the spectrum distribution of the infrared light corresponding to the measured temperature, and identifying the substance to be identified by employing the specified spectrum distribution.

When the component measuring apparatus includes the distance measuring units for measuring the respective distances from the light receiving units 101a and 101b to the measurement object 103, the signal processing unit 104 specifies the distances measured by the distance measuring units. Furthermore, the signal processing unit 104 may specify, from the identification object information, the spectrum distributions corresponding to the specified distances, and may execute the identification operation by employing the specified spectrum direction.

According to this embodiment, in consideration of the fact that the relationship between a radiation rate and wavelength is different depending on substances, the substance (or the component) to be identified, which radiates infrared light at the measured position of the measurement object 103, can be identified by measuring, e.g., the intensity (spectrum distribution) of the infrared light radiated from the measurement object 103.

Each of the light receiving units 101a and 101b includes a light receiving sensor (not illustrated), and an optical system for introducing the infrared light radiated from the measurement object 103 to the light receiving sensor. For example, a condensing optical system including a convex lens and a concave mirror is used as the optical system. The optical system may include a mechanism that changes the distance between the condensing optical system and the light receiving sensor. Such a mechanism enables a measurement target range (band) to be changed.

The following description is made in connection with an example in which the substance (or the component) predetermined to be identified in the component measuring apparatus 100 according to this embodiment is water. A method for identifying whether water is contained in the measurement object 103 or not, by employing the component measuring apparatus 100 according to this embodiment is further described. Regarding water ($H_2O$), it is known that an infrared light radiation rate in a band of 6 to 7 μm is lower than that in a band of 8 to 12 μm. It is also known that a temperature of water can be specified by measuring the intensity of the infrared light radiated from water and falling in a wavelength band of 8 to 12 μm.

In the above-mentioned case, the memory of the signal processing unit 104 stores the identification object information including information as to, e.g., such a magnitude relationship that the intensity of the infrared light including the wavelength in the band of 6 to 7 μm is lower than the intensity of the infrared light including the wavelength in the band of 8 to 12 μm.

The light receiving unit 101a measures the intensity of the infrared light (first received-light intensity) in the band of 6 to 7 μm, which has passed through the optical filter 102a. On the other hand, the light receiving unit 101b measures the intensity of the infrared light (second received-light intensity) in the band of 8 to 12 μm, which has passed through the optical filter 102b.

The signal processing unit 104 compares the intensities (radiant quantities) of the infrared lights, which have been measured by the light receiving units 101a and 101b, and identifies whether water is contained at the measured position of the measurement object 103.

Figure 2A:
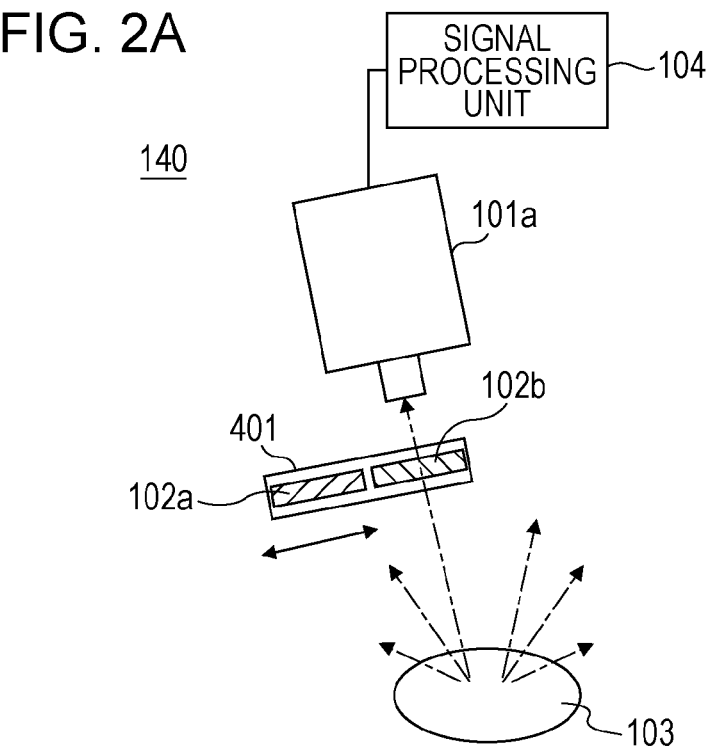
FIG. 2A is a schematic view illustrating another example of the component measuring apparatus according to the first embodiment of the present disclosure.

The component measuring apparatus according to the first embodiment is constituted by employing the light receiving units 101a and 101b. FIG. 2A is a schematic view illustrating another example of the component measuring apparatus according to the first embodiment. In FIG. 2A, a sweeping unit 401 changes the positions of the optical filters 102a and 102b. In a state illustrated in FIG. 2A, the optical filter 102b is arranged at a position (between the measurement object 103 and the light receiving unit 101a in the illustrated example) where part of the infrared light radiated from the measurement object 103 and directing mainly toward the light receiving unit 101a, passes. On the other hand, the optical filter 102a is not arranged at the position where part of the infrared light radiated from the measurement object 103 and directing mainly toward the light receiving unit 101a passes. In the state illustrated in FIG. 2A, therefore, even if there is infrared light passing through the optical filter 102a, the light receiving unit 101a does not receive that infrared light.

Figure 2B:
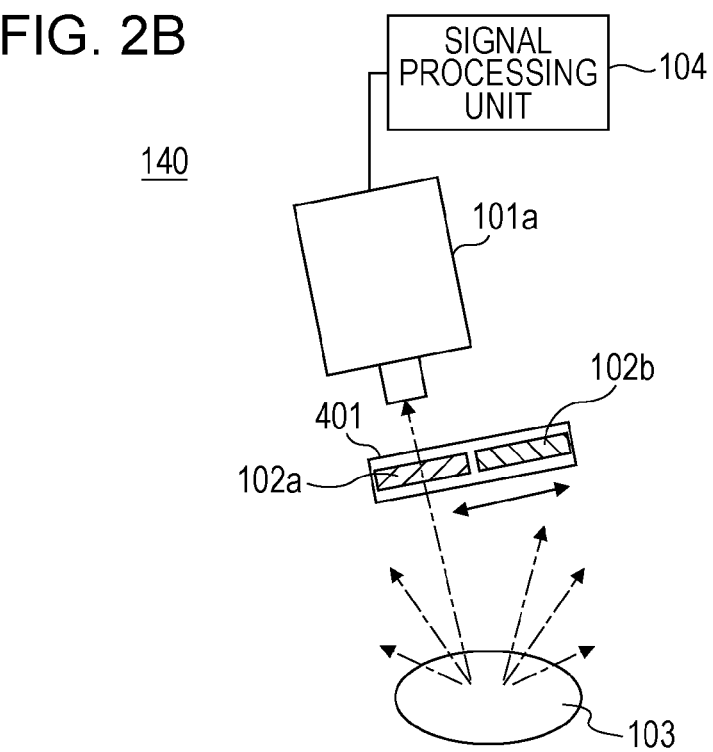
FIG. 2B is a schematic view illustrating the other example of the component measuring apparatus according to the first embodiment of the present disclosure.

FIG. 2B is a schematic view illustrating the other example of the component measuring apparatus according to the first embodiment in a different state from FIG. 2A By operating the sweeping unit 401, the positions of the optical filters 102a and 102b, illustrated in FIG. 2A, are moved such that the state illustrated in FIG. 2B is resulted.

In the state illustrated in FIG. 2B, the optical filter 102a is arranged at the position (between the measurement object 103 and the light receiving unit 101a in the illustrated example) where part of the infrared light radiated from the measurement object 103 and directing mainly toward the light receiving unit 101a passes. On the other hand, the optical filter 102b is not arranged at the position where part of the infrared light radiated from the measurement object 103 and directing mainly toward the light receiving unit 101a passes. In the state illustrated in FIG. 2B, therefore, even if there is infrared light passing through the optical filter 102b, the light receiving unit 101a does not receive that infrared light.

By operating the sweeping unit 401 again, the positions of the optical filters 102a and 102b, illustrated in FIG. 2B, are moved such that the state illustrated in FIG. 2A is resulted.

In a component measuring apparatus 140 illustrated in FIGS. 2A and 2B, the wavelength of the infrared light entering the light receiving unit 101a can be changed by operating the sweeping unit 401 and sweeping (moving) the optical filters 102a and 102b. Therefore, infrared lights having different wavelengths can be measured by one light receiving unit 101a.

In the above-described embodiment, respective intensities (spectrum distributions) of partial infrared lights being parts of the infrared light radiated from the measurement object 103 and having two different wavelengths are measured respectively by two types of optical filters (i.e., the optical filters 102a and 102b in this embodiment) that allow different wavelengths to pass therethrough. However, intensities of infrared lights in different wavelength bands may be measured by employing a dichroic mirror witch such a property that transmitted light and reflected light have different wavelengths.

A band pass filter or an edge filter is used as the optical filter.

While FIGS. 2A and 2B have been described in connection with the case using the optical filter 102a as one example of an optical element, the present disclosure is not limited to that case. For example, a diffraction grating may be used as the optical element instead of the optical filter. The term "diffraction grating" implies an optical element including a lattice-like pattern. The term "lattice-like pattern" implies a pattern that is constituted, for example, by arranging linear concave and convex portions in parallel at a constant period (interval).

The diffraction grating includes, for example, a plurality of regions where the lattice-like patterns have different periods. It is here assumed, for example, that the diffraction grating includes a first region and a second region where the lattice-like patterns have different periods. When the first region is arranged at a first predetermined position, for example, the light receiving unit 101a receives partial infrared light (e.g., diffracted light) including the wavelength in the first wavelength band, the partial infrared light being part of infrared light having entered the first region. When the second region is arranged at a second predetermined position, the light receiving unit 101a receives partial infrared light (e.g., diffracted light) including the wavelength in the second wavelength band, the partial infrared light being part of infrared light having entered the second region. It is further assumed that the first region and the second region cannot be arranged respective at the first predetermined position and the second predetermined position at the same time.

In the above case, the sweeping unit 40 moves the diffraction grating such that the first region is arranged at the first predetermined position. At a different time, the sweeping unit 40 moves the diffraction grating such that the second region is arranged at the second predetermined position.

By employing the above-described diffraction grating, an infrared ray introduced to the light receiving unit 101a can be optionally obtained, by operating the sweeping unit 40, as part of infrared light that has entered one of the lattice-like patterns included in the diffraction grating. As a result, the wavelength of the infrared light reaching the light receiving unit 101a can be changed.

While, in the above-described embodiment, the intensities of the infrared lights in two different wavelength bands are compared with each other, intensities of infrared lights in three or more different wavelength bands may be compared with one another. With an increase in the number of wavelength bands to be measured, the cost is increased, but the density of a component to be detected can be measured at higher accuracy.

While the foregoing example has been described in connection with the case where a moisture distribution is measured, it is desired that, in the case of measuring the moisture distribution, at least one (first wavelength band) of the above-described plural wavelength bands falls within the range of 5 to 8 μm. Whether moisture is contained or not can be identified by so setting the first wavelength band.

When the temperature of water to be identified is 100° C. or higher, the first wavelength band is desirably set to be 12 to 15 μm and more desirably 13 to 14 μm.

Furthermore, at least one wavelength band (second wavelength band) desirably falls within the range of 7 to 14 μm. By setting the second wavelength band to that range, the component measuring apparatus can not only identify the component to be detected, but also measure the temperature of the component to be detected.

While it has been described that the intensity of the infrared light in the range of 5 to 8 μm is desirably measured from the viewpoint of utilizing absorption by water near 6 to 7 μm, the present disclosure is not limited to that case. For example, the intensity of the infrared light in a wavelength band including 10 to 14 μm may be measured. This enables a moisture amount to be calculated by utilizing absorption by water, which occurs near 11 to 13 μm. Moreover, the intensity of the infrared light in a wavelength band of 5 to 15 μm may be measured for measurement of temperature.

Desirably, the component measuring apparatus includes (though not illustrated) a unit for heating (or cooling) the measurement object 103. The spectrum distribution radiated from the measurement object 103 varies depending on temperature as well. Therefore, the component measuring apparatus that measures the presence (density) of the component at high accuracy is provided by changing the temperature and measuring the intensity (spectrum distribution) of the infrared light radiated from the measured position of the measurement object 103 at each temperature. For example, an irradiation unit applying visible light or a far infrared ray (far infrared light) is used as the unit for changing the temperature of the measurement object 103.

The component measuring apparatus 100 according to this embodiment is mounted on a pan tilt stage, and the measurement is performed while the apparatus is scanned along two axes, for example, (or while the measured position is changed). Therefore, a two-dimensional distribution of the target component (density) (hereinafter referred to as a "component distribution image") can be obtained by measuring the presence (density) of the component to be detected at each of the measured positions over a two-dimensional region. In this respect, the component distribution image may also be obtained, for example, by employing a light receiving unit, which includes a matrix sensor, as the light receiving unit without scanning the entirety of the component measuring apparatus 100 along two axes.

The scanning type apparatus is desirable from the viewpoint of reducing the cost. On the other hand, the apparatus using the matrix sensor is desirable from the viewpoint of realizing the measurement in real-time motion images.

In this embodiment, the light receiving unit includes a light receiving element that has sensitivity at least in an infrared range, such as a thermopile, a bolometer, or an InSb quantum photodiode containing at least InSb as a main material.

The component measuring apparatus 100 desirably includes an optical system for condensing the infrared light radiated from the measurement object 103 to the light receiving element. The provision of such an optical system increases sensitivity of the component measuring apparatus.

The above-mentioned optical system is constituted as a reflection optical system including a mirror, or a transmission optical system including a lens that is made of materials containing, e.g., silicon, chalcogenide, or polyethylene, and that allows infrared light to pass therethrough.

When water is the target component, a light receiving element for measuring the intensity of the infrared light in a wavelength band within 5 to 8 μm is desirably constituted as an InSb quantum photodiode. This realizes a component measuring apparatus having higher accuracy with quicker measurement.

Furthermore, an inexpensive component measuring apparatus that measures the presence (density) of moisture in the measurement object and the temperature of the measurement object at the same time is obtained by providing not only a light receiving unit that includes the light receiving element constituted as the InSb quantum photodiode, but also a light receiving unit that includes, e.g., a thermopile as the light receiving element, and that measures the intensity of infrared light of 8 to 13 μm.

When water is the component to be identified, the component measuring apparatus desirably includes a humidity measuring unit (not illustrated) for measuring humidity. For example, the signal processing unit 104 can receive information regarding humidity measured by the humidity measuring unit, and can calculate, based on the received information, an attenuation of light caused by moisture in air that is present in an light path between the measurement object 103 and the light receiving unit 101a or in a light path between the measurement object 103 and the light receiving unit 101b. Thus, the signal processing unit 104 can correct, e.g., the data regarding the intensity of the infrared light, the data being received from the light receiving units 101a and 101b. As a result, a moisture amount on the surface or the inside of the measurement object can be measured at higher accuracy.

In addition, the component measuring apparatus desirably includes a distance measuring unit for measuring the distance from each of the light receiving units 101a and 101b to the measurement object 103. The provision of the distance measuring unit enables an amount of moisture in the measurement object to be measured at even higher accuracy. For example, a TOF (Time-of-Flight) range finder or an ultrasonic range finder is used as the distance measuring unit.

(Second Embodiment)

Figure 3:
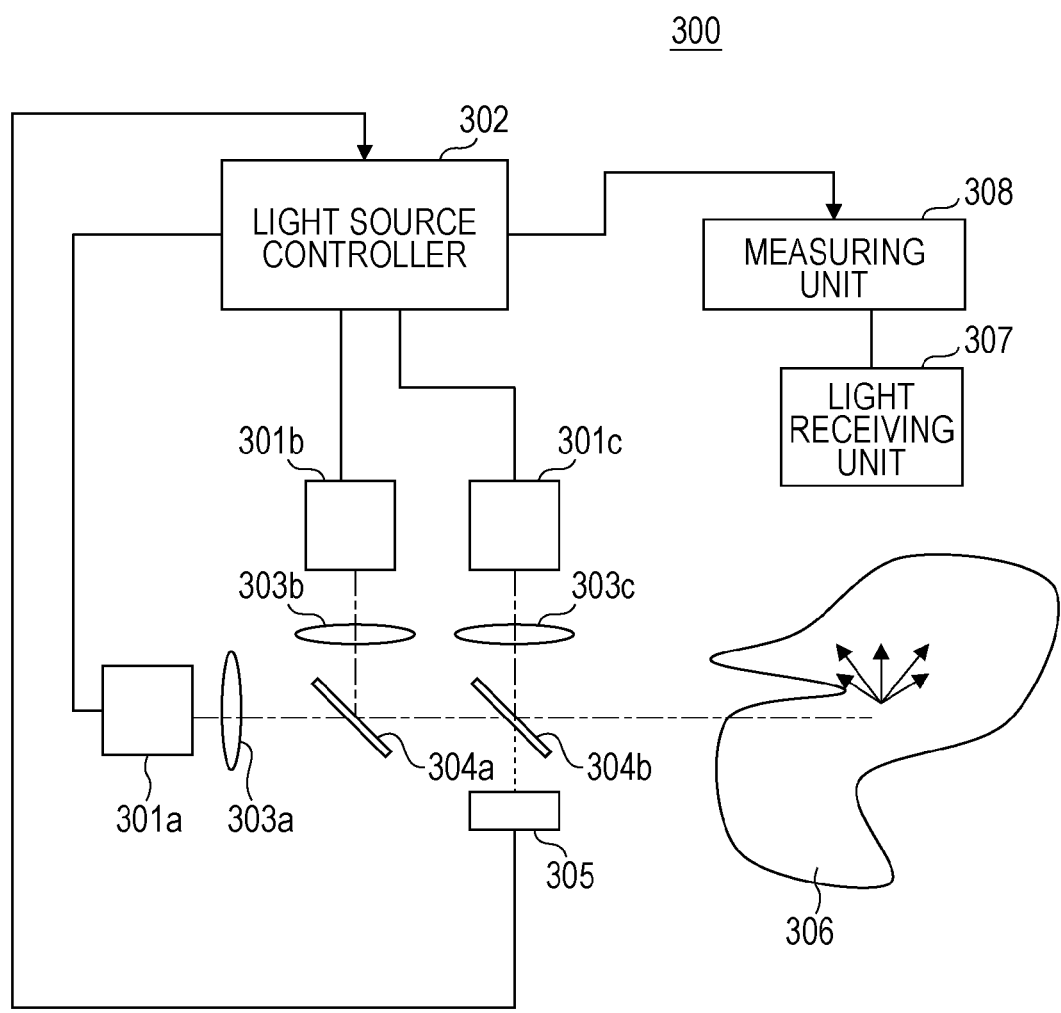
FIG. 3 is a block diagram illustrating one example of a component measuring apparatus according to a second embodiment of the present disclosure.

FIG. 3 is a block diagram illustrating one example of configuration of a component measuring apparatus 300 according to a second embodiment of the present disclosure.

The component measuring apparatus 100 according to this embodiment includes a solid-state light source 301a, a solid-state light source 301b, a solid-state light source 301c, a light source controller 302, a lens 303a, a lens 303b, a lens 303c, a wavelength-sensitivity light branching element 304a, a wavelength-sensitivity light branching element 304b, a forward optical monitor 305, a light receiving unit 307, and a measuring unit 308.

In more detail, reference symbol 301a denotes a solid-state light source that outputs light of a wavelength $\lambda 1$, 301b denotes a solid-state light source that outputs light of a wavelength $\lambda 2$, and 301c denotes a solid-state light source that outputs light of a wavelength $\lambda 3$.

For example, a light emitting diode, a semiconductor laser, or a super-luminescent diode can be used as each of the solid-state light sources 301a to 301c. The wavelengths $\lambda 1$, $\lambda 2$ and $\lambda 3$ are different from one another. In the case using a light emitting diode or a super-luminescent diode, because a wavelength range of emitted light is wide, the wavelength range may be narrowed by employing a filter.

Reference symbol 302 denotes a light source controller that drives the solid-state light sources 301a to 301c. The light source controller 302 drives successively the solid-state light sources 301a to 301c with modulation, for example. Moreover, 303a to 303c denote lenses through which the lights emitted from the solid-state light sources 301a to 301c are converted to substantially parallel lights.

For example, the light source controller 302 includes a memory (not illustrated) and a processor (not illustrated), such as a central processing unit (CPU). The CPU reads a light source controlling program from the memory and executes the light source controlling program. The light source controller 302 is realized by the CPU executing the light source controlling program stored in the memory.

Alternatively, a function of the light source controller 302 may be implemented by dedicated hardware circuits (or dedicated hardware circuitry), such as application-specific integrated circuit (ASICs) or field programmable gate arrays (FPGAs).

Reference symbols 304a and 304b denote wavelength-sensitivity light branching elements each of which may be provided as, e.g., a dichroic mirror or a dichroic prism.

The wavelength-sensitivity light branching element 304a allows the light of the wavelength $\lambda 1$ to pass therethrough and reflects the light of the wavelength $\lambda 2$. The wavelength-sensitivity light branching element 304b allows the lights of the wavelength $\lambda 1$ and $\lambda 2$ to pass therethrough and reflects the light of the wavelength $\lambda 3$.

After entering the measurement object 306 via the wavelength-sensitivity light branching element 304b, the lights of the wavelengths $\lambda 1$, $\lambda 2$ and $\lambda 3$ are absorbed or diffused in the measurement object 306. Part of the light having been diffused in the measurement object 306 is output as scattered light from the measurement object 306.

While three solid-state light sources are used in the above description, the present disclosure can provide a small-sized component measuring apparatus, which is able to perform spectrometry, by employing at least two solid-state light sources that have different wavelengths.

The number of solid-state light sources can be increased by adding the wavelength-sensitivity light branching element. Reference symbol 305 denotes the forward optical monitor for monitoring not only intensities of the lights of the wavelengths $\lambda 1$ and $\lambda 2$, which are slightly reflected by the wavelength-sensitivity light branching element 304b, but also intensity of the light of the wavelength $\lambda 3$, which slightly passes through the wavelength-sensitivity light branching element 304b, and for feeding-back the monitored light intensities to the light source controller 302. In accordance with the intensity of the fed-back light, the light source controller 302 controls respective outputs of the solid-state light sources 301a to 301c to be held constant. After entering the measurement object 306 via the wavelength-sensitivity light branching element 304b and having been absorbed or diffused in the measurement object 306, the lights of the wavelengths $\lambda 1$, $\lambda 2$ and $\lambda 3$ are partly output as scattered lights from the measurement object 306.

The light receiving unit 307 receives the lights scattered from the measurement object 306 and inputs the intensity of the received lights to the measuring unit 308. The measuring unit 308 stores the intensities of the received lights and executes arithmetic processing. Drive information regarding signals for driving the solid-state light sources 301a to 301c is also input to the measuring unit 308 from the light source controller 302.

For example, the measuring unit 308 includes a memory (not illustrated) and a processor (not illustrated), such as a central processing unit (CPU). The CPU reads a measuring program from the memory and executes the measuring program. The measuring unit 308 is realized by the CPU executing the measuring program stored in the memory.

Alternatively, a function of the measuring unit 308 may be implemented by dedicated hardware circuits (or dedicated hardware circuitry), such as application-specific integrated circuit (ASICs) or field programmable gate arrays (FPGAs).

With the configuration described above, the solid-state light sources 301a to 301c having known output wavelengths are successively driven with modulation, and the scattered lights generated after having been absorbed in the measurement object 306 are received by the light receiving unit 307. Furthermore, drive information of the solid-state light sources 301a to 301c (e.g., the intensities of the respective lights output from the solid-state light sources 301a to 301c) and the intensities of the lights received by the light receiving unit 307 are combined (linked) with each other in the measuring unit 308. As a result, an absorption spectrum of the measurement object 306 can be obtained in a discrete fashion.

As one example, an absorption spectrum (first absorption spectrum) corresponding to the wavelength $\lambda 1$ is obtained from the difference between the intensity of the light of the wavelengths $\lambda 1$, which is output from the solid-state light source 301a, and the intensity of the light of the wavelengths $\lambda 1$, which is received by the light receiving unit 307.

As another example, an absorption spectrum (second absorption spectrum) corresponding to the wavelength $\lambda 2$ is obtained from the difference between the intensity of the light of the wavelengths $\lambda 2$, which is output from the solid-state light source 301b, and the intensity of the light of the wavelengths $\lambda 2$, which is received by the light receiving unit 307.

As still another example, an absorption spectrum (third absorption spectrum) corresponding to the wavelength $\lambda 3$ is obtained from the difference between the intensity of the light of the wavelengths $\lambda 3$, which is output from the solid-state light source 301c, and the intensity of the light of the wavelengths $\lambda 3$, which is received by the light receiving unit 307.

On the other hand, the memory of the measuring unit 308 previously stores the identification object information regarding the intensities of the lights received by the light receiving unit 307 when the lights of the wavelengths $\lambda 1$, $\lambda 2$ and $\lambda 3$ are applied to the substance (or the component) to be identified.

Furthermore, the memory of the measuring unit 308 may previously store, as the identification object information, data regarding the absorption spectra, which correspond to the lights of the wavelengths $\lambda 1$, $\lambda 2$ and $\lambda 3$ and which are calculated from the intensities of the lights received by the light receiving unit 307 when the lights of the wavelengths $\lambda 1$, $\lambda 2$ and $\lambda 3$ are applied to the substance (or the component) to be identified while an amount of the substance (or the component) to be identified is changed.

The identification object information may contain, as data, the intensity of the light of the wavelength $\lambda 1$ (first reference light intensity), for example, obtained when the light of the wavelength $\lambda 1$ output from the solid-state light source 301a is applied to the substance (or the component) to be identified and the light from the substance is received by the light receiving unit 307 in advance.

On that occasion, in both the cases where the light of the wavelength $\lambda 1$ is applied to the measurement object 306 and is applied to the substance to be identified in advance, the intensities of the light of the wavelength $\lambda 1$ emitted from the solid-state light source 301a in those cases are set to values that are the same or that can be regarded as being the same.

The identification object information may further contain, as data, the intensity of the light of the wavelength $\lambda 2$ (second reference light intensity), for example, obtained when the light of the wavelength $\lambda 2$ output from the solid-state light source 301b is applied to the substance (or the component) to be identified and the light from the substance is received by the light receiving unit 307 in advance.

On that occasion, in both the cases where the light of the wavelength $\lambda 2$ is applied to the measurement object 306 and is applied to the substance to be identified in advance, the intensities of the light of the wavelength $\lambda 2$ emitted from the solid-state light source 301b in those cases are set to values that are the same or that can be regarded as being the same.

The identification object information may further contain, as data, the intensity of the light of the wavelength $\lambda 3$ (third reference light intensity), for example, obtained when the light of the wavelength $\lambda 3$ output from the solid-state light source 301c is applied to the substance (or the component) to be identified and the light from the substance is received by the light receiving unit 307 in advance.

On that occasion, in both the cases where the light of the wavelength $\lambda 3$ is applied to the measurement object 306 and is applied to the substance to be identified in advance, the intensities of the light of the wavelength $\lambda 3$ emitted from the solid-state light source 301c in those cases are set to values that are the same or that can be regarded as being the same.

Moreover, the identification object information may contain, as data, the absorption spectrum (first reference absorption spectrum) obtained from the intensity of the light of the wavelength $\lambda 1$ when the light of the wavelength $\lambda 1$ output from the solid-state light source 301a is applied to the substance (or the component) to be identified and the light from the substance is received by the light receiving unit 307 in advance.

The identification object information may further contain, as data, the absorption spectrum (second reference absorption spectrum) obtained from the intensity of the light of the wavelength $\lambda 2$ when the light of the wavelength $\lambda 2$ output from the solid-state light source 301b is applied to the substance (or the component) to be identified and the light from the substance is received by the light receiving unit 307 in advance.

The identification object information may further contain, as data, the absorption spectrum (third reference absorption spectrum) obtained from the intensity of the light of the wavelength $\lambda 3$ when the light of the wavelength $\lambda 3$ output from the solid-state light source 301c is applied to the substance (or the component) to be identified and the light from the substance is received by the light receiving unit 307 in advance.

The measuring unit 308 identifies the presence (density) of the substance (or the component) to be identified at a position where the lights from the solid-state light sources 301a to 301c are applied (i.e., at a measuring point), by employing the discrete absorption spectra obtained from the light receiving unit 307 and the light source controller 302.

One specific operation example of identification executed by the measuring unit 308 is as follows. When the identification object information contains respective values of the first reference light intensity, the second reference light intensity, and the third reference light intensity, the measuring unit 308 calculates an absolute value (first absolute value) of the difference between the intensity of the light of the wavelengths $\lambda 1$, which is received by the light receiving unit 307, and the first reference light intensity, an absolute value (second absolute value) of the difference between the intensity of the light of the wavelengths $\lambda 2$, which is received by the light receiving unit 307, and the second reference light intensity, and an absolute value (third absolute value) of the difference between the intensity of the light of the wavelengths $\lambda 3$, which is received by the light receiving unit 307, and the third reference light intensity.

If the first absolute value, the second absolute value, and the third absolute value are smaller than respective preset thresholds, the measuring unit 308 determines that the substance (or the component) to be identified is contained at the position where the lights from the solid-state light sources 301a to 301c are applied (i.e., at the measuring point). If not so, the measuring unit 308 determines that the substance (or the component) to be identified is not contained.

When the measuring unit 308 determines that the substance (or the component) to be identified is contained, it can further execute the following operation.

When the identification object information contains data linking the amount of the substance (or the component) to be identified with the respective absorption spectra for the lights of the wavelengths $\lambda 1$, $\lambda 2$ and $\lambda 3$, which spectra are calculated from the intensities of the lights received by the light receiving unit 307, the measuring unit 308 may specify the combination of the first reference light intensity, the second reference light intensity, and the third reference light intensity in which the first absolute value, the second absolute value, and the third absolute value are smaller than the respective preset thresholds, and may determine the amount of the substance to be identified, which amount is linked with the absorption spectra calculated from the specified combination, as an amount of the measurement object 306.

Another specific operation example of identification executed by the measuring unit 308 is as follows. When the identification object information contains respective values of the first reference absorption spectrum, the second reference absorption spectrum, and the third reference absorption spectrum, the measuring unit 308 calculates an absolute value (fourth absolute value) of the difference between the first absorption spectrum and the first reference absorption spectrum, an absolute value (fifth absolute value) of the difference between the second absorption spectrum and the second reference absorption spectrum, and an absolute value (sixth absolute value) of the difference between the third absorption spectrum and the third reference absorption spectrum.

If the fourth absolute value, the fifth absolute value, and the sixth absolute value are smaller than respective preset thresholds, the measuring unit 308 determines that the substance (or the component) to be identified is contained at the position where the lights from the solid-state light sources 301a to 301c are applied (i.e., at the measuring point). If not so, the measuring unit 308 determines that the substance (or the component) to be identified is not contained.

When the identification object information contains data linking the amount of the substance (or the component) to be identified with the respective absorption spectra for the lights of the wavelengths λ1, λ2 and λ3, which spectra are calculated from the intensities of the lights received by the light receiving unit 307, the measuring unit 308 may specify the combination of the first reference absorption spectrum, the second reference absorption spectrum, and the third reference absorption spectrum in which the fourth absolute value, the fifth absolute value, and the sixth absolute value are smaller than the respective preset thresholds, and may determine the amount of the substance to be identified, which amount is linked with the specified combination, as an amount of the measurement object 306.

Thus, the measuring unit 308 can measure the component (component density) existing at the position where the lights from the solid-state light sources are applied (i.e., at the measuring point), by measuring the discrete absorption spectra (i.e., the difference in absorptions at plural wavelengths).

When the substance (or the component) to be identified is water, for example, it is known that absorption rates of water are different for lights of different wavelengths in a 1500-nm band, a 1300-nm band, and a 900-nm band. In view of such a property, for example, the wavelength λ1 of the light emitted from the solid-state light source 301a is set to 1500 nm, the wavelength λ2 of the light emitted from the solid-state light source 301b is set to 1300 nm, and the wavelength λ3 of the light emitted from the solid-state light source 301c is set to 900 nm.

The memory of the measuring unit 308 previously stores the identification object information corresponding to the wavelengths λ1, λ2 and λ3 for a predetermined amount of water. When the predetermined amount of water is present plural, the memory may previously store the identification object information corresponding to the wavelengths λ1, λ2 and λ3 for each of the plural predetermined amounts of water.

The measuring unit 308 can determine whether water exists at the measuring point, and can obtain an amount of the water, for example, by combining the drive information of the solid-state light sources 301a to 301c with the intensities of the lights received by the light receiving unit 307, and by employing resulting discrete absorption spectra.

Furthermore, by continuing the above-described measurement, the measuring unit 308 can identify the presence or the absence of water at the measuring point, and can measure changes in amount of the identified water with the lapse of time.

By successively driving the solid-state light sources 301a to 301c with modulation and inputting a modulation signal to the measuring unit 308, the measuring unit 308 can amplify and measure weak scattered light in accordance with the known lock-in amplification technique, and can increase a signal-to-noise ratio. The signal input to the measuring unit 308 for the lock-in amplification can also be obtained from the forward optical monitor 305.

While modulation frequencies used for driving the solid-state light sources 301a to 301c may be the same with only phases shifted differently, the modulation frequencies can also be set different from one another. By setting the modulation frequencies to be different from one another, it is possible to increase a degree of separation in the lock-in amplification and to facilitate wavelength discrimination in comparison with the case of shifting only the phases at the same modulation frequency.

By driving the solid-state light sources 301a to 301c in turn, the absorption spectrum can be obtained by employing only one light receiving unit 307, and the apparatus size can be reduced. Moreover, since the lights emitted from the solid-state light sources can be guided to propagate coaxially by employing the wavelength-sensitivity light branching element while the number of the solid-state light sources is increased in scalable design, scalability can be ensured for wavelength, and the lights can be applied to the same position of the measurement object 306.

By employing the solid-state light source, high-speed modulation can be realized unlike the case using, e.g., a lamp-type optical source as in a related-art spectrometer. Furthermore, by modulating the solid-state light sources 301a to 301c and amplifying signal light in accordance with the lock-in amplification technique, stable measurement can be realized even under the presence of disturbance light.

While, in the embodiment described above, the light received by the light receiving unit 307 is the scattered light from the measurement object 306, the difference in absorption depending on wavelength can also be of course determined by that the light receiving unit 307 receives light having transmitted through the measurement object 306.

While, in the embodiment described above, the solid-state light sources 301a to 301c are individual light sources that are physically separated from one another, the plural solid-state light sources may be constituted by providing a plurality of emitters on one semiconductor chip, or by employing a wavelength variable semiconductor laser that can output lights of different wavelengths in accordance with external control.

The component measuring apparatus desirably includes a confocal optical system coupling the measurement object 306 and the light receiving unit 307. Power of light emitted from an arbitrary point on the surface of the measurement object 306 can be measured with the provision of the confocal optical system. By measuring the intensity of light per emission position in the measurement object 306, an absorption spectrum in the measurement object can be obtained at higher accuracy.

The component measuring apparatus may be constituted such that at least one of the position where the light enters the measurement object 306 and the position where the light emitted and propagated via the confocal optical system arrives at the light receiving unit 307 is movable. With that feature, an absorption spectrum distribution inside the measurement object 306 can be obtained, and the component density distributed inside the measurement object can be determined at each depth ranging from the surface to the deep inside of the measurement object.

By branching the light emitted from the solid-state light source into two beams, applying one beam to the measurement object, and making the other beam interfere with the light having returned from the measurement object, an absorption spectrum of only light having returned from an arbitrary depth (position) inside the measurement object can be determined. As a result, a distribution of component density can be measured at each depth inside the measurement object.

In the component measuring apparatus 300 according to the present disclosure, the position of the measuring point (i.e., the point where the light from the solid-state light source is applied) can be changed by mounting the component measuring apparatus 300 on a pan tilt stage, or by disposing a polygon mirror or a two-axis scanning MEMS (Micro Electro Mechanical System) mirror between the wavelength-sensitivity light branching element 304b and the measurement object 306.

By thus performing the component measurement while the measuring point is changed, a component distribution (density distribution) of the object component can be determined.

For example, a distribution image of component density can also be displayed by scanning the measuring point along two axes, converting the component density at each position to luminance and color information, and displaying the converted data. (Hereinafter, a scan range of the measuring point is referred to as a measuring area.)

Figure 4:
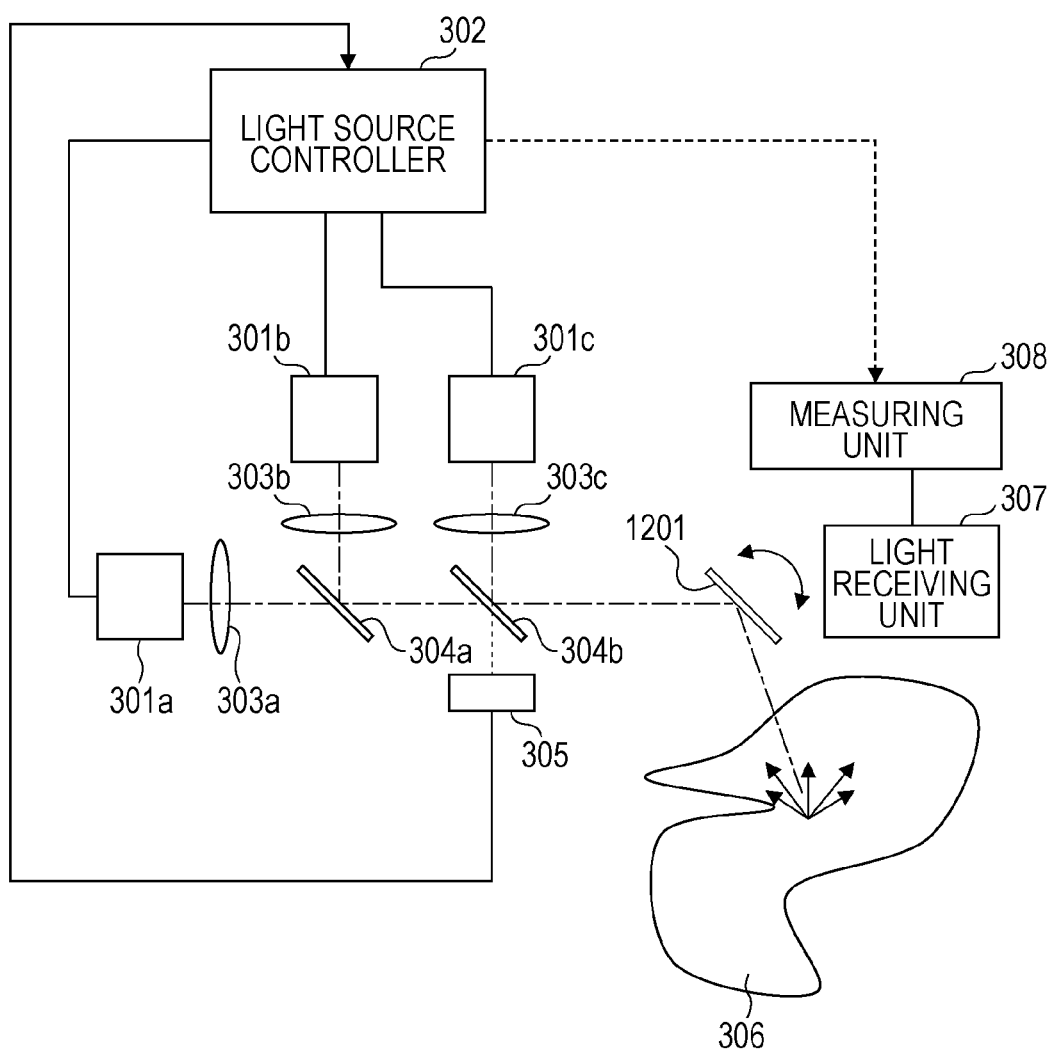
FIG. 4 is a block diagram illustrating another example of the component measuring apparatus according to the second embodiment of the present disclosure.

FIG. 4 is a block diagram illustrating another example of the component measuring apparatus according to the second embodiment of the present disclosure.

A component measuring apparatus 1200 illustrated in FIG. 4 includes a scanning mirror 1201 between the wavelength-sensitivity light branching element 304b and the measurement object 306 such that the position of the measuring point (i.e., the point where the light from the solid-state light source is applied) can be changed. By performing the component measurement while the measuring point is changed, a component density distribution (image information) of the object component can be determined.

A method employing the pan tilt stage can measure the component density distribution more inexpensively with high sensitivity. On the other hand, a method employing the scanning mirror can measure the component density distribution at a higher speed.

For example, a polygon mirror or a two-axis scanning MEMS mirror is used as the scanning mirror 1201.

By converting the component density at each measuring point to luminance and color information, the component density distribution (image information) can be presented to a user. When lights of plural wavelengths are applied to the measuring point while the measuring point is changed by employing the scanning mirror or the pan tilt stage, there is available a method of turning on the lights of plural wavelengths at the same time, or a method of successively turning on the lights of plural wavelengths in a time division manner.

The method of turning on the lights of plural wavelengths at the same time enables the component density distribution to be measured at a higher speed. The method of successively turning on the lights of plural wavelengths in a time division manner is desired for the reason that the component density distribution can be measured more inexpensively.

In the method of successively turning on the lights of plural wavelengths in a time division manner, each light source is desirably turned on while the scanning mirror or the pan tilt stage is scanned. This enables the component density distribution to be measured at a high speed even with the successively turning-on method as with the simultaneously turning-on method.

In the case of employing the successively turning-on method and turning the light sources while the scanning mirror is driven, it is desired that incident angles of the plural lights (laser beams) of different wavelengths upon the scanning mirror are set different from one another. With that feature, the component measuring apparatus can be designed such that the laser beams turned on at different times are applied to the same measuring point, and the component density distribution can be measured at a higher S/N ratio.

It is also desirable to provide a unit for adjusting the incident angle of the light from each light source upon the scanning mirror. With the provision of such a unit, a component densitometer is obtained which can measure the component density at a high S/N ratio even when a measuring speed or a measuring range is changed.

The component measuring apparatus 300 according to the present disclosure desirably includes a visible camera having sensitivity in a wavelength band of 300 nm to 1100 nm, a thermograph having sensitivity in a wavelength band of 8 $\mu$m to 13 $\mu$m, or an image capturing unit (camera) such as a near infrared camera. In other words, the component measuring apparatus 300 desirably captures an image of the measuring area where the component density distribution is to be measured.

With that feature, an object having entered the measuring area can be detected by employing background differential information of motion images obtained with the image capturing unit.

By confirming the object (dynamic body) having entered the measuring area, only changes of component distribution in a portion of the measuring area other than the dynamic body can be detected.

(Third Embodiment)

A moving body 501 for measuring a component distribution in a room is described in a third embodiment.

Figure 5:
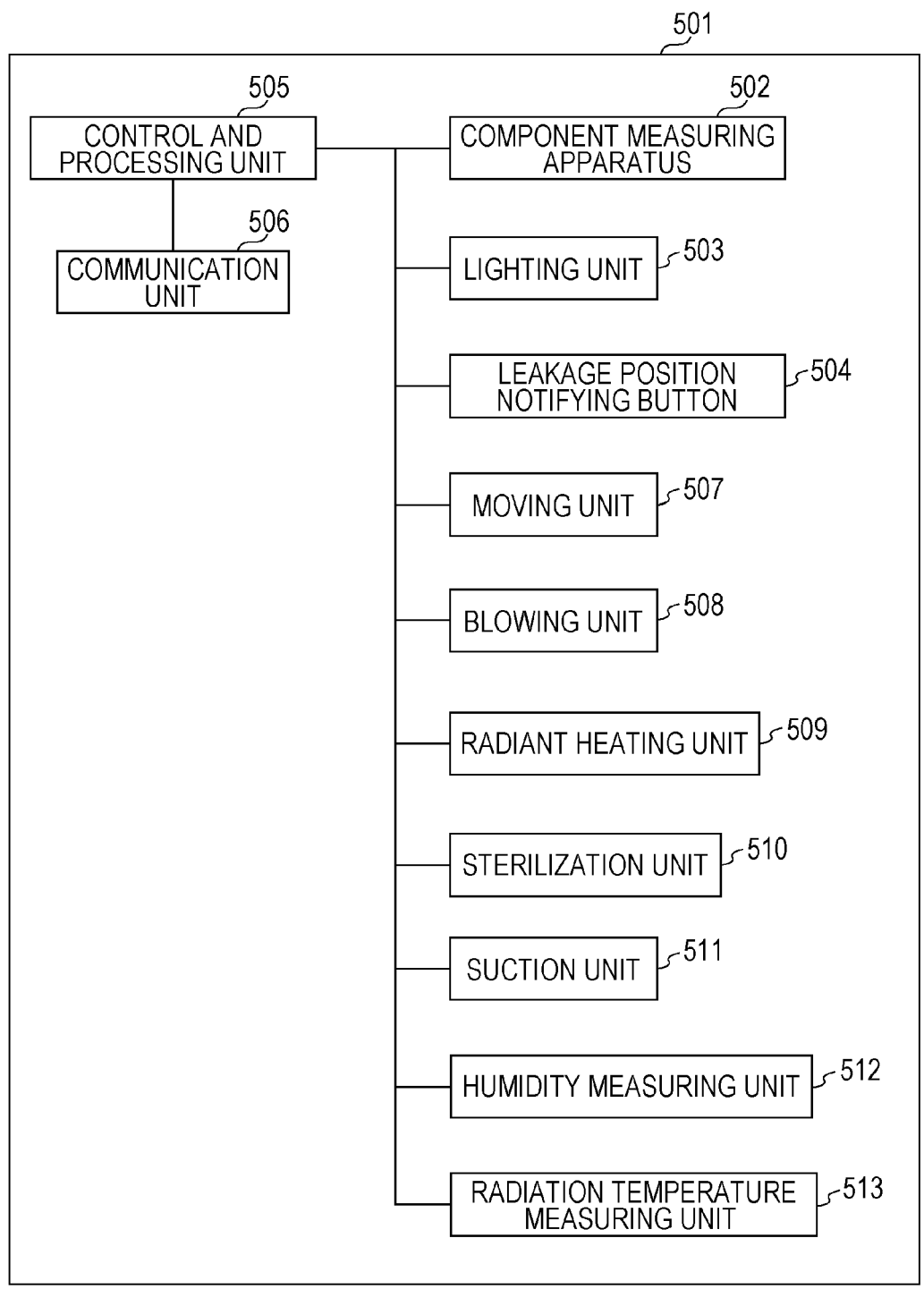
FIG. 5 is a functional block diagram illustrating one example of a moving body according to a third embodiment of the present disclosure.

FIG. 5 is a functional block diagram illustrating one example of the moving body according to the third embodiment of the present disclosure. The moving body according to this embodiment is featured in including one of the component measuring apparatuses described above in the first and second embodiments.

As illustrated in FIG. 5, the moving body 501 includes a component measuring apparatus 502, a lighting unit 503, a leakage position notifying button 504, a control and processing unit 505, a communication unit 506, a moving unit 507, a blowing unit 508, a radiant heating unit 509, a sterilization unit 510, a suction unit 511, a humidity measuring unit 512, and a radiation temperature measuring unit 513.

For example, the moving body 501 includes a memory (not illustrated) and a processor (not illustrated), such as a central processing unit (CPU). The CPU reads a program from the memory and executes the program. The control and processing unit 505 is realized by the CPU executing the program.

Alternatively, a function of the control and processing unit 505 may be implemented by dedicated hardware circuits (or dedicated hardware circuitry), such as application-specific integrated circuit (ASICs) or field programmable gate arrays (FPGAs).

For example, the control and processing unit 505 controls a component measuring apparatus 502, a lighting unit 503, a communication unit 506, a moving unit 507, a blowing unit 508, a radiant heating unit 509, a sterilization unit 510, a suction unit 511, a humidity measuring unit 512, and a radiation temperature measuring unit 513.

For example, when the user pushes the leakage position notifying button 504, the control and processing unit 505 controls the moving unit 507.

It is to be noted that the moving body 501 is not always required to include the lighting unit 503, the leakage position notifying button 504, the communication unit 506, the moving unit 507, the blowing unit 508, the radiant heating unit 509, the sterilization unit 510, the suction unit 511, the humidity measuring unit 512, and the radiation temperature measuring unit 513.

Figure 6:
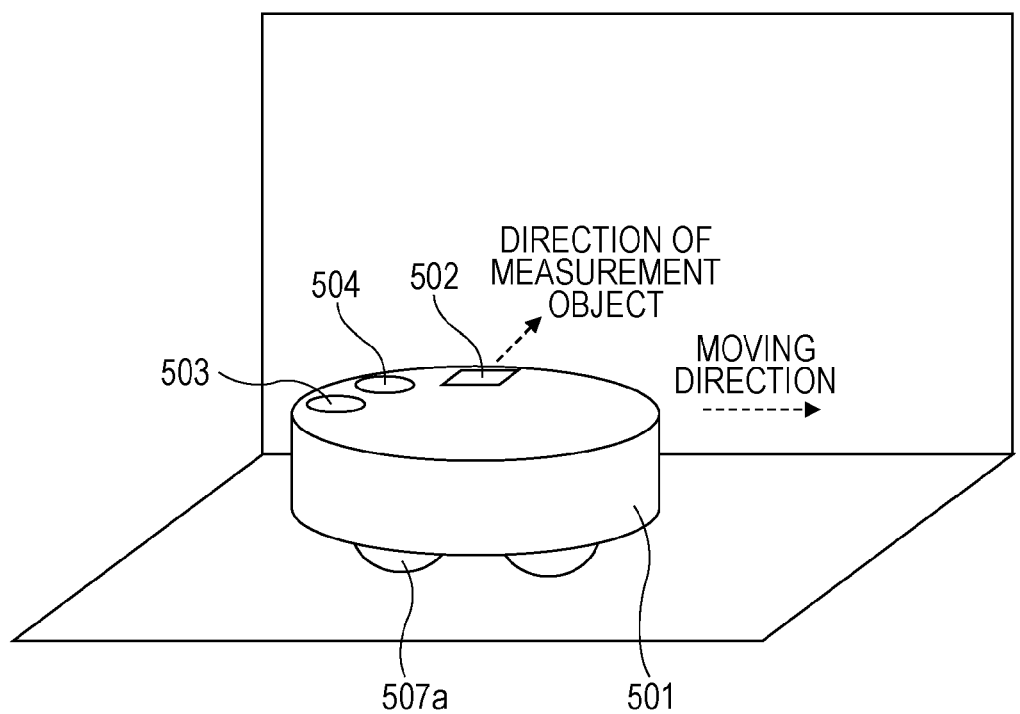
FIG. 6 is a perspective view illustrating one example of an external appearance of the moving body according to the third embodiment of the present disclosure.

FIG. 6 is a perspective view illustrating one example of an external appearance of the moving body according to the third embodiment.

As illustrated in FIGS. 5 and 6, the moving body 501 according to this embodiment is a moving body including the component measuring apparatus 502. The component measuring apparatus 502 is desirably the component measuring apparatus 100 described in the first embodiment or the component measuring apparatus 300 described in the second embodiment. With the component measuring apparatus 100 or the component measuring apparatus 300 mounted on the moving body 501, a component distribution in a certain place, such as a room, can be measured while the moving body 501 is moving in the room.

Because the moving body 501 having the above-described configuration measures a component to be identified at a plurality of places in a room while moving in the room, a distribution of the component to be identified can be measured at the plural places in the room over a widely spreading region.

For example, when the component to be identified by the component measuring apparatus 502 is "moisture", the component measuring apparatus 502 functions as a moisture measuring unit, and it can measure a moisture distribution (presence of moisture) at a wetted place in the room. A method for identifying moisture by the component measuring apparatus 502 is as per described above in the first embodiment or the second embodiment.

The component measuring apparatus 502 may measure a distribution of pollen or virus in the room, as another example of the component to be identified, at the measuring place. Alternatively, the component measuring apparatus 502 may measure a concentration distribution of formaldehyde, as still another example of the component to be identified, at the measuring place.

The control and processing unit 505 corresponding to the controller periodically moves the moving body 501 in the room by controlling the moving unit 507 (e.g., actuation of a motor, directions of wheels 507a) at intervals of a preset time. The control and processing unit 505 may control the component measuring apparatus 502 to perform the measurement of the component distribution.

Furthermore, the component distribution in the room can be periodically measured by checking whether at least a part (desirably the whole) of a movable region of the moving body 501 is wetted.

The control and processing unit 505 may control the moving unit 507 to move the moving body 501 and may control the component measuring apparatus 502 to measure the component distribution in the room on the "day of the week" or at the "time of the day" designated by the user. That feature enables the component distribution in the room to be measured on the "day of week" or at the "time of day" at which the user is especially anxious about the component distribution.

More desirably, a moisture distribution in the room is measured in the early morning. Because the early morning (before the sunrise) is a time zone in which dew condensation is most apt to occur in a day, a region in the room where mold tends to generate can be detected with high sensitivity.

The control and processing unit 505 may control the component measuring apparatus 502 to measure the component distribution at all times while the moving body 501 is moving. Alternatively, the control and processing unit 505 may control the moving unit 507 to move the moving body 501 to a target place and, after stopping the moving body 501, may control the component measuring apparatus 502 to measure the component distribution.

The moving body 501 according to this embodiment further includes the suction unit 511 (not illustrated in FIG. 6) that sucks (takes in) wastes, such as dust and dirt, in the room while the moving body 501 is moving. With that feature, the moving body 501 can perform not only the measurement of the moisture distribution in the room, but also cleaning of the room. In such a case, the control and processing unit 505 controls the timing of the measurement of the moisture distribution and the timing of the cleaning. For example, when the moisture distribution in the room is measured in the early morning, the relevant constituent members may be controlled to perform only the measurement of the moisture distribution in the early morning, and to perform the cleaning in a different time zone. That setting is effective in avoiding disturbance of sleep, namely in keeping the user from being wakened up by noise that is generated during the cleaning. When there is no necessity of sucking (taking in) wastes, such as dust and dirt, in the room by employing the moving body 501, the moving body 501 is not always required to include the suction unit 511.

The moving body 501 further includes the communication unit 506 utilizing WiFi or Bluetooth (registered trademark), for example. The communication unit 506 may include communication circuit utilizing WiFi or Bluetooth (registered trademark). The control and processing unit 505 can control, e.g., the time at which the component distribution is to be measured, based on information obtained through the communication unit 506 from the outside. For example, when the moving body 501 can obtain, through the communication unit 506, information regarding, e.g., power-on history of illumination in the user's bed room or history of the time of use of a smartphone, it is possible to estimate a life pattern of the user based on the history of the wake-up time and the bedtime, the time of use of the smartphone, etc. Accordingly, the moving body 501 can set the cleaning time and the time of measuring the component distribution in the room in match with the estimated life pattern of the user. When there is no necessity of obtaining information from the outside by employing the moving body 501, the moving body 501 is not always required to include the communication unit 506.

For example, the cleaning is desirably performed while the user is away from home, and the measurement of the moisture distribution is most desirably performed before the sunrise and before the user wakes up. Whether the user is away from home can be determined from position information of a smartphone of the user, and information regarding the daily wake-up time can be obtained from the on/off history of illumination in the bedroom. Information of a schedule book of the user is also desirably obtained through the communication unit 506. By grasping days in which the user wakes up different times, such as business trip days, based on the schedule information, the wake-up time of the user can be determined more correctly. Daily information regarding the weather, the atmospheric temperature, and the humidity are further desirably obtained in addition to the sunrise time. From that daily information, the moisture distribution in the room can be measured at a date where dew condensation is more apt to occur (e.g., at a time where the humidity is high, a time where the atmospheric temperature is low, or a time before the sunrise). This results in that a risk of the generation of mold can be grasped with a smaller number of measurements and can be informed to the user at earlier timing. In addition, a distance through which the moving body 501 is moved for the measurements can be reduced, and power consumption can be reduced.

The moving unit 507 or the suction unit 511 may be controlled in accordance with the information regarding moisture in an object, which has been measured by the moisture measuring unit. For example, the moving unit 507 is controlled such that the moving body 501 will not move over an object containing a certain amount or more of moisture. Alternatively, the suction unit 511 may be controlled such that the suction unit 511 will not perform the suction in regions around the object containing a certain amount or more of moisture. This can eliminate the problem such as clogging caused when the suction unit 511 sucks a liquid or the object containing a large amount of moisture.

The moving body 501 according to this embodiment may further include a drying unit that, when dew condensation in the room is detected as a result of measuring the moisture distribution, removes (or dries) the detected dew condensation. By carrying out the drying in addition to detection of the dew condensation, the generation of mold can be prevented. The drying unit may be the radiant heating unit 509 that radiates a far infrared ray, or the blowing unit 508 that blows hot air. The drying can be practiced more inexpensively. When there is no necessity of removing (drying) the dew condensation by employing the moving body 501, the moving body 501 is not always required to include the drying unit.

The moving body 501 according to this embodiment further includes the sterilization unit 510 for sterilizing germs. For example, the sterilization unit 510 can prevent the generation of mold, for example, by applying an ultraviolet ray or ions to a wetted region. The sterilization unit 510 can prevent the generation of germs with smaller power consumption than the case using the drying unit. On the other hand, the drying unit is able to prevent the generation of mold in, e.g., grooves at peripheral edges of a room into which the ultraviolet ray cannot be directly applied. As a matter of course, it is desirable to include both the drying unit and the sterilization unit.

When there is no necessity of sterilizing germs by employing the moving body 501, the moving body 501 is not always required to include the sterilization unit 510.

The control and processing unit 505 in the moving body 501 according to this embodiment may control the individual constituent members such that, when wetting, e.g., dew condensation, is detected in the room, the control and processing unit 505 completes the measurement of the component distribution in the entirety of the room without starting the drying (sterilization) at once, and after moving the moving body 501 again to the place where the wetting has been detected, performs the drying (sterilization). With that control, the drying (sterilization) can be performed in a place where dew condensation is seriously generated (e.g., a place where wetting occurs over a wide region) with priority.

The control and processing unit 505 may control the moving body 501 such that, after completing the measurement of the component distribution in the room, the moving body 501 is returned for charging to a place where a charger is installed, in order to perform the charging required to carry out the drying and the sterilization. After the end of the charging, the control and processing unit 505 moves the moving body 501 to the place where the wetting has been detected, and then performs the drying (sterilization). With that feature, a greater drying (sterilization) effect can be realized with a battery having a smaller capacity, and a reduction in size and cost of the moving body can be obtained.

The moving body 501 may store, in a memory (not illustrated), information regarding the place where the dew condensation (wetting) has been detected once. By storing such information, the moving body 501 can recognize, as an easily wetting place, the place where the dew condensation (wetting) has been detected once.

When the dew condensation (wetting) has been detected in the same place at different times, the moving body 501 may accumulate, in the memory, information regarding the number of the detections in a way linked with information regarding the place where the dew condensation (wetting) has been detected. By accumulating such information, the moving body 501 can recognize, as an easily wetting place, the place where the dew condensation (wetting) has been detected, for example, in a predetermined number or more.

The control and processing unit 505 may control the moving unit 507 to visit the easily wetting place (in a larger number than visiting to other places), and may control the component measuring apparatus 502 to make confirmation (component measurement) as to whether the relevant place is wetted or not. With that control, the place wetted in the room can be confirmed with smaller power consumption than the case of confirming the entirety room at a high frequency.

The moving body 501 according to this embodiment may include the communication unit 506 and may communicate with another device in the room through the communication unit 506 when the dew condensation has been detected, thereby operating the other device to remove the dew condensation. For example, the moving body 501 may control another device (e.g., an air conditioner having the dehumidifying function or a dehumidifier), which also has a communication unit and a drying unit, based on information regarding a room, a position in the room, and time in which and at which the dew condensation occurs. Using the other device equipped in the room, as described above, is desirable for the reason that the generation of mold in home can be prevented by an inexpensive moving body, which does not include the drying unit and the sterilization (disinfection) unit 510 in itself.

The generation of mold may be prevented through irradiation with an ultraviolet ray or ions, for example, by employing another device equipped in the room as in the above-described case.

The moving body 501 according to this embodiment desirably further includes a notification unit for notifying the component distribution representing, e.g., the wetted places in the room, to the user. With the provision of such a notification unit, the user can confirm the component distribution (distribution of the wetted places) in the room. As a result, the user can take an action to prevent the generation of mold, for example, by ventilating the room.

When there is no necessity of notifying the component distribution representing, e.g., the wetted places in the room, to the user by employing the moving body 501, the moving body 501 is not always required to include the notification unit.

One example of the notification unit for notifying the distribution of the wetted places in the room to the user will be described below.

The moving body 501 may include the lighting unit 503, e.g., an LED, as one example of the notification unit. When a wetted region is detected, the control and processing unit 505 may notify the user of the fact that the wetted region is present (has been present) in the room, for example, by controlling the lighting unit 503 to be turned on. With that notification, the user can confirm the presence of the wetted region in the room with no need of special operation.

The moving body 501 may include, e.g., the leakage position notifying button 504 in the notification unit. For example, when the user pushes the leakage position notifying button 504, the control and processing unit 505 controls the moving unit 507 such that the moving body 501 is moved to a position in the room where the wetting has been detected, the position being recorded in the memory (not illustrated). With the movement of the moving body 501, the wetted position can be notified to the user. Thus, the user can confirm the wetted position at desired timing (in a free time).

A method for notifying the leakage position to the user may be practiced by notifying information of the leakage position to an information display unit by employing the communication unit 506 in the moving body 501. For example, a user's smartphone having a display or a TV is used as the information display unit.

Figure 7:
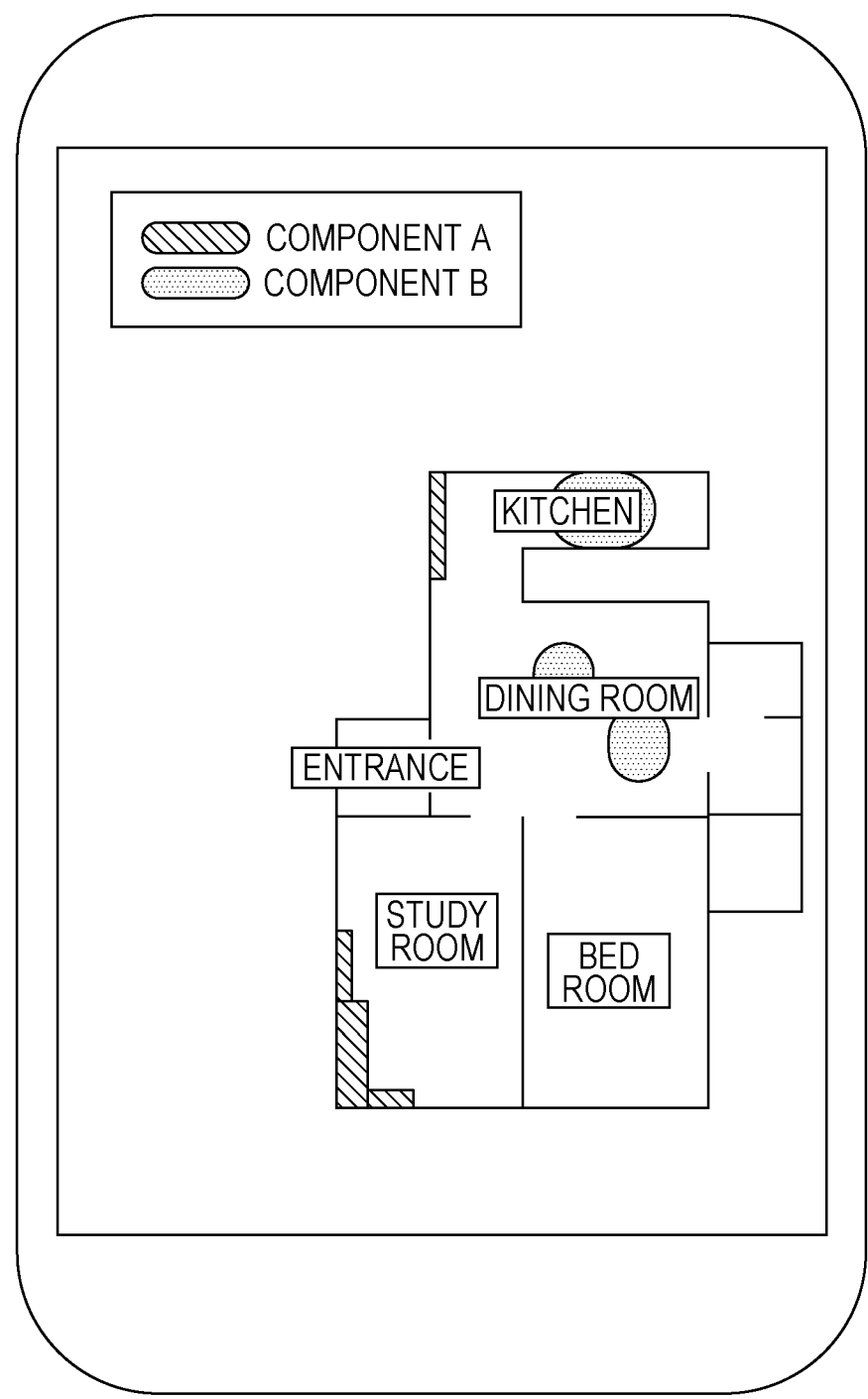
FIG. 7 illustrates one example of a component distribution presenting screen in the third embodiment of the present disclosure.

FIG. 7 illustrates one example of a component distribution presenting screen represented on a display.

When notification to the user is performed by employing the information display unit, the image illustrated in FIG. 7 may be represented on the display for notifying the wetted position to the user. As illustrated in FIG. 7, it is possible to display a map of rooms where the moving body is disposed and movable, and to display positions, at which the components are present, in the map for each component based on the component distribution.

A pattern or a color, for example, may be changed per component. Even the same component may be expressed, for example, by changing the size or fatness of a displayed mark depending on an amount of the relevant component. As a result, the user can more easily recognize the component distribution in the room.

Individual places on the map may be previously named by a "kitchen", a "dining room", etc., and the moving body 501 may notify the information of the component distribution to the user in voices speaking by using a speaker (not illustrated) included in the moving body 501, e.g., "In this morning, moisture was detected at the west side in the kitchen". Thus, the user can recognize the component distribution in the room without operating the information presenting unit.

The naming per place on the map may be performed by manual inputting by the user. As an alternative, a name estimated from the shape of each room or the positional relationship among rooms may be presented to the user, and if the presented name is not proper, the user may correct that name.

The moving body 501 according to this embodiment may further include a humidity sensor corresponding to the humidity measuring unit 512 that measures humidity, and a radiation thermometer corresponding to the radiation temperature measuring unit 513 that measures radiation temperature. This enables the easily wetting place in the room to be determined more inexpensively. More specifically, it is possible to calculate the dew point in the room from the result measured by the humidity sensor, to detect a portion of a wall or a floor in the room where a temperature is lower than or close to the dew point, and to calculate humidity near such a portion of the wall or the floor. Thus, the place where dew condensation tends to occur can be determined even under condition that the dew condensation does not occur.

An electric humidity sensor or a dew-point humidity sensor is used as the humidity sensor. The electric humidity sensor is more suitable because a higher-speed humidity sensor is desirable. By employing the electric humidity sensor, a state tending to cause the dew condensation can be more accurately determined even when the moving body moves at a high moving speed.

For example, a thermopile or a bolometer having sensitivity for a far infrared ray is used as the radiation thermometer.

When there is no necessity of measuring the humidity by employing the moving body 501, the moving body 501 is not always required to include the humidity measuring unit 512.

Furthermore, when there is no necessity of measuring the radiation temperature by employing the moving body 501, the moving body 501 is not always required to include the radiation temperature measuring unit 513.

The moisture measuring unit (component measuring apparatus 502) may include both the humidity measuring unit 512 and the radiation temperature measuring unit 513.

Figure 8:
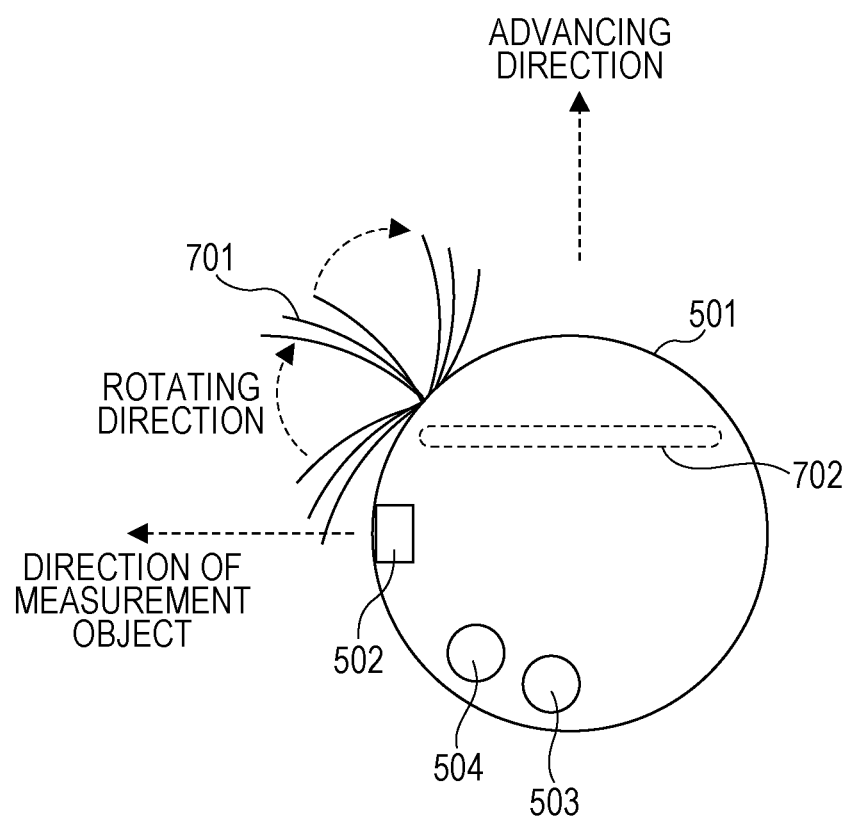
FIG. 8 is a plan view illustrating another example of the external appearance of the moving body according to the third embodiment of the present disclosure.

FIG. 8 is a plan view illustrating another example of the external appearance of the moving body 501 according to the third embodiment.

As illustrated in FIG. 8, the moving body 501 according to this embodiment may include a rotating brush 701. The rotating brush 701 is desirably mounted in the same side as the component measuring apparatus 502 with respect to an advancing direction of the moving body 501. With such an arrangement, the component can be measured at peripheral edges (walls) of a room while dust at the peripheral edges of the room is swept by the rotating brush 701. The effect of preventing the generation of mold in a room can be increased by measuring the component on walls at peripheral edges of the room where mold, etc. are most apt to generate with dew condensation, etc.

The rotating brush 701 is desirably mounted forward of the component measuring apparatus 502 in the advancing direction thereof. With such an arrangement, dust can be prevented from adhering to the component measuring apparatus 502, and the measurement accuracy can be maintained for a longer term.

The moving body 501 further includes a dust suction opening 702 in a bottom surface. The suction unit is disposed inside the moving body 501, and it sucks (takes in) wastes, such as dust and dirt, through the dust suction opening 702. A rotating direction of the rotating brush 701 is desirably set such that the rotating brush 701 is rotated to pass the component measuring apparatus 502, the wall, and the bottom surface of the moving body 501 (i.e., the dust suction opening 702) in the mentioned order. As a result, dust can be prevented from adhering to the component measuring apparatus 502, and the measurement accuracy can be maintained for an even longer term.

(Fourth Embodiment)

A drying method of measuring a dried condition of a wetted substance such as washing (hereinafter referred to as a "drying target"), and controlling environments where the drying target is present (such as an air direction, an air speed, temperature, humidity, and luminance) is described in a fourth embodiment.

The following description is made about a drying machine 801 as one example of carrying out the drying method according to this embodiment.

Figure 9:
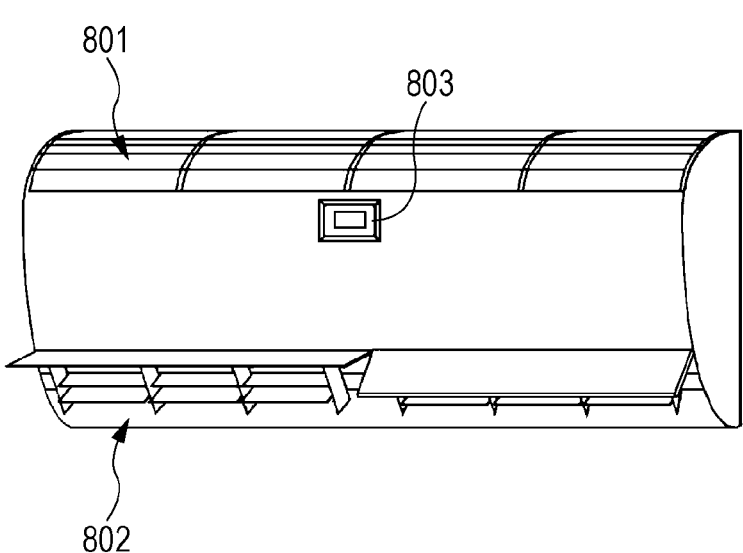
FIG. 9 illustrates one example of an external appearance of a drying machine according to a fourth embodiment of the present disclosure.
Figure 9:
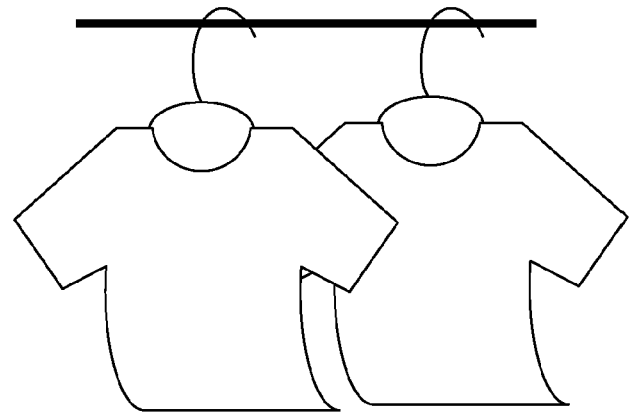

FIG. 9 is a perspective view illustrating one example of an external appearance of the drying machine 801 according to the fourth embodiment.

Figure 10:
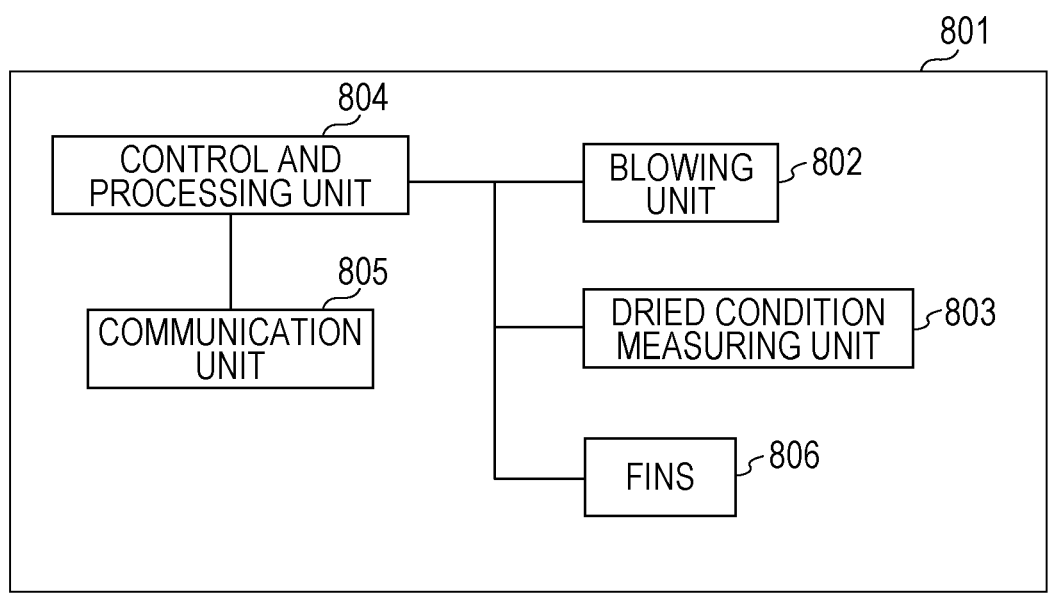
FIG. 10 is a functional block diagram illustrating one example of configuration of the drying machine according to the fourth embodiment of the present disclosure.

FIG. 10 is a functional block diagram illustrating one example of configuration of the drying machine 801 according to the fourth embodiment.

As illustrated in FIG. 9, the drying machine 801 according to this embodiment includes a blowing unit 802 and a dried condition measuring unit 803 that measures a dried condition of the drying target. As illustrated in FIG. 10, the drying machine 801 further includes a control and processing unit 804 and a communication unit 805.

For example, the drying machine 801 includes a memory (not illustrated) and a processor (not illustrated), such as a central processing unit (CPU). The CPU reads the program from the memory and executes the program. The control and processing unit 804 is realized by the CPU executing the program.

Alternatively, a function of the control and processing unit 804 may be implemented by dedicated hardware circuits (or dedicated hardware circuitry), such as application-specific integrated circuit (ASICs) or field programmable gate arrays (FPGAs).

For example, the control and processing unit 804 controls the blowing unit 802 the dried condition measuring unit 803, the communication unit 805, the fan and the fins 806.

Moreover, a fan and fins 806 are disposed inside the drying machine 801. A temperature of air blown from the blowing unit 802 can be adjusted by adjusting a temperature of the fins 806. For example, a heater, a Peltier element, or a compressor is used as a unit for adjusting the temperature of the fins 806.

The drying machine 801 may be connected to an outdoor unit.

A speed of air blown from the blowing unit 802 can be adjusted by adjusting a rotating speed of the fan mounted inside the drying machine 801.

The humidity and the temperature of the air blown from the blowing unit 802 can be adjusted independently, for example, by incorporating two types of the fins 806 of which temperatures are independently adjustable.

The dried condition measuring unit 803 is constituted as the component measuring apparatus 100 described in the first embodiment or the component measuring apparatus 300 described in the second embodiment. By setting moisture as the object component to be measured, it is possible to confirm a position of the drying target around the drying machine 801, and to determine an amount of moisture contained in the drying target.

In accordance with information obtained from the dried condition measuring unit 803 with respect to the position of the drying target, the control and processing unit 804 controls the blowing unit 802 such that blown air is concentrated only to an area where the drying target is present. As a result, the drying target can be dried in a shorter time. When the drying target is washing, proliferation of germs is suppressed to a lower level as a time taken for drying is shorter.

It is desirable that the time taken for drying can be set by the user. To that end, the drying machine 801 may include a user interface, such as a touch panel or a switch, through which the user can input the drying time or the time of end of drying. With that feature, the user can adjust the drying time in consideration of the schedule of the user and the schedules of the user's family.

In accordance with information regarding the amount of moisture in each drying target, it is possible to confirm the drying target in which the amount of remaining moisture is large, and to blow air in a concentrated manner such that the drying target taking a longer time for drying can also be dried in a shorter time.

A radiation thermometer, such as a thermopile or a bolometer, may be used as the dried condition measuring unit 803. The temperature of a wetted substance is lower than that of the surroundings because the wetted substance is deprived of evaporation heat. Therefore, a wetted place can be inexpensively determined by employing the radiation thermometer as the dried condition measuring unit 803. However, it is desirable to employ, as the dried condition measuring unit 803, the component measuring apparatus 100 described in the first embodiment or the component measuring apparatus 300 described in the second embodiment, and to measure a moisture distribution. The reason is that the amount of moisture can be measured more accurately.

When the drying machine 801 according to this embodiment is used to fulfill the other function than the function of drying the drying target, the drying machine 801 may be designed to additionally include a washing drying mode, e.g., a control mode for performing the drying method described above in this embodiment, such that the user can freely select such a control mode.

The control and processing unit 804 may set a time during which air is blown to only an upper portion or a lower portion of the drying target after start of the drying, and may control the individual constituent members to blow air in such a manner. The control and processing unit 804 may obtain the measurement result from the dried condition measuring unit 803 at proper timings, and may determine a drying speed of each drying target. Thus, the control and processing unit 804 can determine the drying speed of each drying target at earlier timing and can dry the drying target in a shorter time by controlling air to be blown to only a limited portion in a concentrated manner. A time during which air is blown to only the limited portion in a concentrated manner is desirably set in a time zone as early as possible after start of the drying. In other words, such a time zone is desirably set at least within one hour after start of the drying.

The drying machine 801 according to this embodiment desirably includes a cover (antifouling cover) covering the dried condition measuring unit 803 to prevent fouling of a driving portion, a light receiving surface, a light emitting surface, etc. of an infrared detection unit that constitutes the dried condition measuring unit 803.

The antifouling cover is desirably controlled by a unit for detecting the presence or the absence of a person such that the antifouling cover covers the dried condition measuring unit 803 only when the person is present nearby. With that feature, the person is released from the trouble of removing the antifouling cover each time the person goes out.

When the dried condition measuring unit 803 is installed in a bathroom, it is desired that the drying machine 801 includes a unit for detecting whether water is running out from a shower or a faucet, and that the antifouling cover covers the dried condition measuring unit 803 while water is running out. As a result, fouling of the dried condition measuring unit can be prevented.

In the above-described case, the antifouling cover is set in place when water is running out. In another example, however, the antifouling cover may be set in place only when a water flow is a predetermined value or more. The dried condition can be measured when a possibility of fouling with water splashes is low.

The antifouling cover desirably includes a humidity sensor for measuring humidity, and covers the dried condition measuring unit 803 when the measured humidity is a predetermined value or more. With that feature, the dried condition measuring unit can be prevented from being fouled with dew condensation.

The dried condition measuring unit 803 desirably includes a heating unit. By heating the light receiving surface and the light emitting surface, the fouling with dew condensation can be prevented more effectively.

While the above embodiment has been described in connection with the drying machine 801 including both the dried condition measuring unit 803 and the blowing unit 802, an apparatus including the dried condition measuring unit 803 may be separate from an apparatus including the blowing unit 802 (involving other units, such as fins, a fan, a Peltier element, and a heater, for adjusting temperature, humidity, air direction, and air speed). Those apparatuses include respective communication units and are operated in a linked manner. As a result, the above-described drying method using the drying machine 801 can be practiced in this embodiment.

(Fifth Embodiment)

Figure 11:
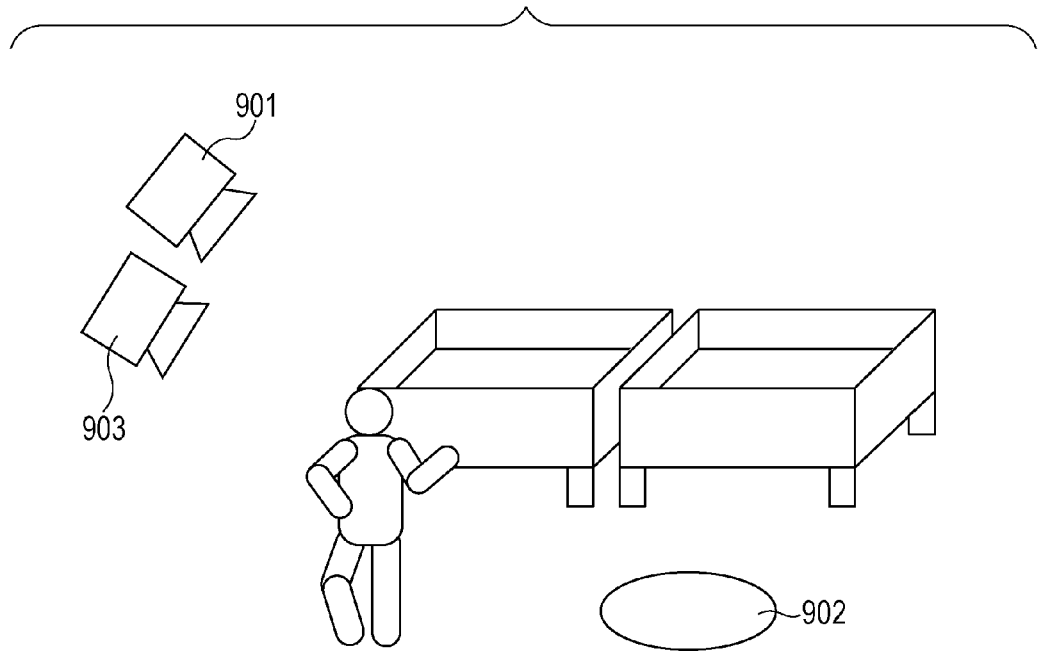
FIG. 11 illustrates one example of a positional relationship between a measurement object and a component measuring apparatus according to a fifth embodiment of the present disclosure.
Figure 12:
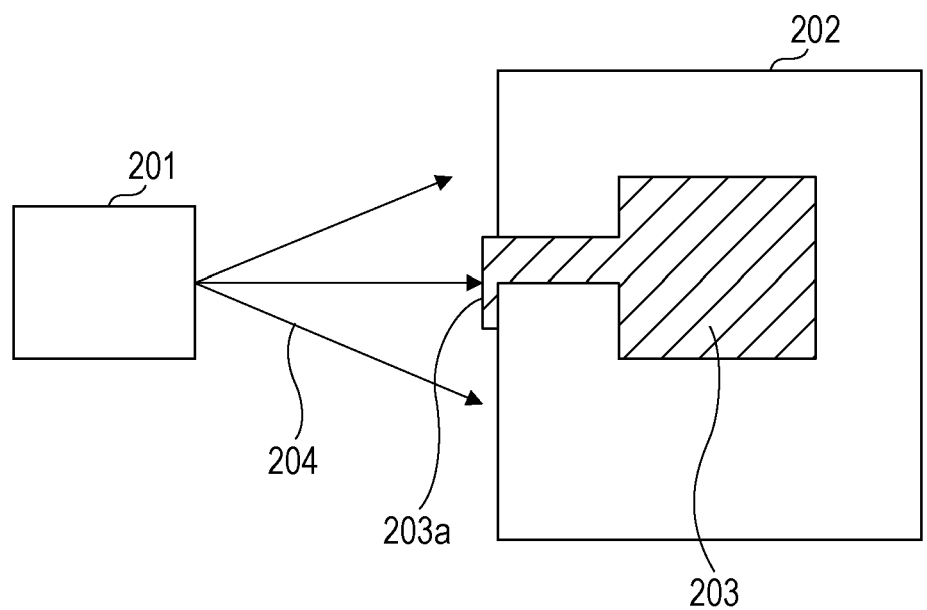
FIG. 12 is a schematic view illustrating a liquid leakage detection device of related art.

FIG. 11 illustrates one example of a positional relationship between a measurement object and a component measuring apparatus according to a fifth embodiment of the present disclosure.

The fifth embodiment represents the case where, as illustrated in FIG. 11, water wetting 902 on a floor surface is detected by employing a component measuring apparatus 901 such as described above in the first or second embodiment.

A floor surface of a store selling fresh foods, etc. is set as a measuring area. When the water wetting 902 on the floor surface is detected, the detected result is notified to a store worker. Therefore, the store worker can notice the water wetting on the store floor at earlier timing. For example, the store worker can wipe out the water wetting to avoid an accident that a customer falls down on the wetted floor of the store.

In this embodiment, a problem arises in that, because customers walk across the measuring area, coming-in of a person is detected as the presence of the water wetting on the floor surface (namely, the water wetting is falsely detected) even if a water density in the measuring area is just continuously measured. Such false detection may occur because moisture is present on the surface of the human skin.

To cope with the above-mentioned problem, an image capturing device (camera) 903 for taking an image of the measuring area is desirably disposed which may be, e.g., a visible camera having sensitivity in a wavelength band of 300 nm to 1100 mm, a thermograph having sensitivity in a wavelength band of 8 µm to 13 µm, or a near infrared camera having sensitivity in a wavelength band of 700 nm to 2 µm. Thus, an image of the measuring area where a distribution of component density is to be measured is desirably taken by the image capturing device 903.

The component measuring apparatus 901 may be wirelessly connected to the image capturing device 903 through a communication unit (not illustrated). As an alternative, the image capturing device 903 and the component measuring apparatus 901 may be connected to each other by a wired signal line. This enables the user to transfer information regarding the position of a dynamic body, etc. without effort. The component measuring apparatus 901 is connected to a control and processing device (not illustrated). The image capturing device 903 may also be connected to the control and processing device (not illustrated). The control and processing device may be disposed in the same space as that where the component measuring apparatus 901 and the image capturing device 903 are present, and may be physically connected to them via cables, for example. Alternatively, the control and processing device may be disposed in an external space, and may be connected to the component measuring apparatus 901 and the image capturing device 903 via communication units.

A person having entered the measuring area can be detected from motion images, which have been obtained with the image capturing device 903, by employing the background different method, for example. Accordingly, the component measuring apparatus 901 can distinguish the position of a person and the position of water based on information obtained with the image capturing device 903.

While the above description is made about the method for detecting an object having entered the measuring area from the motion image information, obtained with the image capturing device 903, by utilizing the background differential method, the object (dynamic body) having entered the measuring area may be detected by performing three-dimensional measurement with, e.g., a Time-of-Flight range finder using a laser beam, or a millimeter wave radar.

It is further desirable to include a unit that determines a relationship between a position (pixel) of the dynamic body, which has been detected by the three-dimensional measurement or the image capturing device, and a position (pixel) in a component distribution image obtained with the component measuring apparatus. With the provision of such a unit, the dynamic body and the water wetting on the floor surface can be distinguished at higher accuracy.

The above-mentioned relationship may be determined by a method of setting a plurality of points as reference marks in the measuring area, and then aligning both the images with each other in advance.

In the case of the component measuring apparatus in which the lights emitted from the solid-state light sources are applied to the floor surface as in the second embodiment, a position of the measuring point (of the component measuring apparatus 901) and a pixel in an image obtained with the image capturing device 903 can be linked with each other by generating, from at least one of the solid-state light sources, light in a band where the image capturing device 903 has sensitivity (i.e., light of 300 nm to 100 nm).

The component measuring apparatus 901 and the image capturing device 903 are desirably installed at positions as close as possible. More specifically, a light receiving unit of the component measuring apparatus 901 and a unit for measuring a position of the dynamic body (i.e., the image capturing device 903) are desirably constituted as an integral unit or positioned adjacent to each other. With such an arrangement, the position of the dynamic body can be determined more accurately.

When the component measuring apparatus is of the scanning type, control is desirably executed such that the scanning is stopped during a period in which the dynamic body is detected, and after the dynamic body is no longer detected, the scanning is started again from the position where the scanning has been stopped. With such control, water wetting in the measuring area can be detected without exception.

While the above embodiment is described in connection with the case of detecting moisture in a certain place where people are present, such as a store, a monitoring device to detect wetting or freezing of a road surface can also be realized with a similar configuration. Dynamic bodies, such as cars, are present on the road surface. Thus, only wetting or freezing of the road surface can be detected by distinguishing the dynamic bodies and the road surface from each other with the similar configuration.

However, when freezing of the road surface is detected, a radiation thermometer for measuring a temperature of the road surface is desirably disposed in addition to the component measuring apparatus for detection of moisture. A wetted state and a frozen state can be distinguished with the provision of the radiation thermometer.

Desirably, a component measuring apparatus that measures both temperature and moisture is used as in the first embodiment. A small-sized and inexpensive apparatus for detecting freezing of the road surface can be provided without need of position alignment between temperature distribution information and moisture distribution information, which are obtained with the component measuring apparatus.

The present disclosure is useful as a component measuring apparatus that measures an infrared ray emitted from an object, and as a component analyzing apparatus and a moving body each of which includes a light source having specified wavelength and which does not need a spectroscopic element. The present disclosure is further useful in such applications as detecting the presence of a specific substance, e.g., water, and visualizing a distribution of the specific substance.

What is claimed is:

1. A moving body comprising:
   a mover that moves the moving body;

a sucker that sucks air and/or a substance existing outside of the moving body;

a moisture measurer that measures information regarding moisture in an object based on received light; and a controller that controls at least one of the mover and the sucker in accordance with the information regarding moisture in the object, wherein the controller executes at least one of (i) controlling the mover not to move over the object when the object includes a first certain amount or more of moisture, and (ii) controlling the sucker not to perform sucking in a region around the object when the object includes a second certain amount or more of moisture.

2. The moving body of claim 1, wherein the moisture measurer includes:

a plurality of light sources having different wavelengths;

an irradiator that applies lights emitted from the plural light sources to the object;

a light receiver that receives at least one of light having transmitted through the object and light having been scattered from the object; and an intensity measurer that measures, per wavelength, intensity of the light received by the light receiver.

3. The moving body of claim 1, wherein the moisture measurer includes a plurality of light receivers that (i) receive infrared lights of different wavelengths radiated from the object, and (ii) measure respective intensities of the infrared lights of different wavelengths.

4. The moving body of claim 1, wherein the moisture measurer (i) includes at least one light receiver that receives infrared lights having different wavelengths radiated from the object, and (ii) changes the wavelength of the infrared light entering the at least one light receiver.

5. The moving body of claim 1, further including a humidity measurer that measures humidity, and a radiation temperature measurer that measures radiation temperature.

6. The moving body of claim 1, further including a dryer that dries a place where presence of moisture has been confirmed by the moisture measurer.

7. The moving body of claim 6, wherein the dryer dries the place by at least one of (i) radiating a far infrared ray and (ii) blowing hot air.

8. The moving body of claim 1, further including a notifier that notifies a user of the place where the presence of moisture has been confirmed by the moisture measurer.

9. The moving body of claim 8, wherein the notifier includes a button to be pushed by the user, and when the user pushes the button, the moving body is moved to a place where moisture is present, the place being recorded in the moving body, thus notifying the user of the place where moisture is present.

10. The moving body of claim 1, wherein the sucker is disposed inside the moving body and sucks dust and/or dirt through a suction opening formed in the moving body, and the moisture measurer measures the information regarding moisture in the object that is positioned in a direction different from an advancing direction of the moving body.

11. The moving body of claim 1, further including:

a communicator that obtains status of use of another device; and a controller that sets at least one of a time at which the moving body is to be moved by the mover, and a time at which moisture is to be measured by the moisture measurer, in accordance with the status of use of the other device, the status being obtained through the communicator.

12. The moving body of claim 1, further including a sterilizer that sterilizes a place where the presence of moisture has been confirmed by the moisture measurer.

13. The moving body of claim 12, wherein the sterilizer sterilizes the place by applying an ultraviolet ray or ions.

\* \* \* \* \*